(12) United States Patent
Anis et al.

(10) Patent No.: US 10,410,743 B2
(45) Date of Patent: Sep. 10, 2019

(54) SYSTEM AND METHOD FOR ELECTRONIC COMMUNICATION

(71) Applicant: Medsol LLC, Leesburg, VA (US)

(72) Inventors: Ather Anis, Leesburg, VA (US); Waqas Ahmad, Leesburg, VA (US)

(73) Assignee: Bond Investments, LLC, Ashburn, VA (US)

( * ) Notice: Subject to any disclaimer, the term of this patent is extended or adjusted under 35 U.S.C. 154(b) by 213 days.

(21) Appl. No.: 15/595,605

(22) Filed: May 15, 2017

(65) Prior Publication Data

US 2017/0329906 A1 Nov. 16, 2017

Related U.S. Application Data

(60) Provisional application No. 62/336,849, filed on May 16, 2016.

(51) Int. Cl.

| | |
|---|---|
| *G06F 15/16* | (2006.01) |
| *G16H 10/60* | (2018.01) |
| *G06F 21/30* | (2013.01) |
| *G06F 21/62* | (2013.01) |
| *G06F 19/00* | (2018.01) |
| *G06Q 10/10* | (2012.01) |
| *G06Q 50/24* | (2012.01) |

(52) U.S. Cl.
CPC ............ *G16H 10/60* (2018.01); *G06F 19/00* (2013.01); *G06F 21/30* (2013.01); *G06F 21/6245* (2013.01); *G06Q 10/10* (2013.01); *G06Q 50/24* (2013.01)

(58) Field of Classification Search
CPC ......... G16H 10/60; G06F 19/00; G06F 21/30; G06F 21/6245; G06Q 10/10; G06Q 50/24
See application file for complete search history.

(56) References Cited

U.S. PATENT DOCUMENTS

| | | | |
|---|---|---|---|
| 2004/0034550 A1* | 2/2004 | Menschik | G16H 10/60 705/3 |
| 2014/0122125 A1* | 5/2014 | Deshpande | G06F 19/3418 705/3 |
| 2014/0275849 A1* | 9/2014 | Acquista | A61B 5/0022 600/301 |
| 2015/0056576 A1* | 2/2015 | Nikolskiy | A61C 13/0004 433/214 |

* cited by examiner

*Primary Examiner* — Richard G Keehn
(74) *Attorney, Agent, or Firm* — Rahman LLC

(57) ABSTRACT

A system for enabling management and sharing of health records of a first user with a second user, wherein system includes a health record upload module that enables uploading of the health record onto a central repository, and a health record sharing module that enables the first user to select the second user from a list of a plurality of users and share the uploaded health record with the second user. The system is further configured with an interface that enables the first user to post any a combination of a comment, an image, a discussion topic, an update, a message, and a reply message.

11 Claims, 23 Drawing Sheets

FIG. 8B

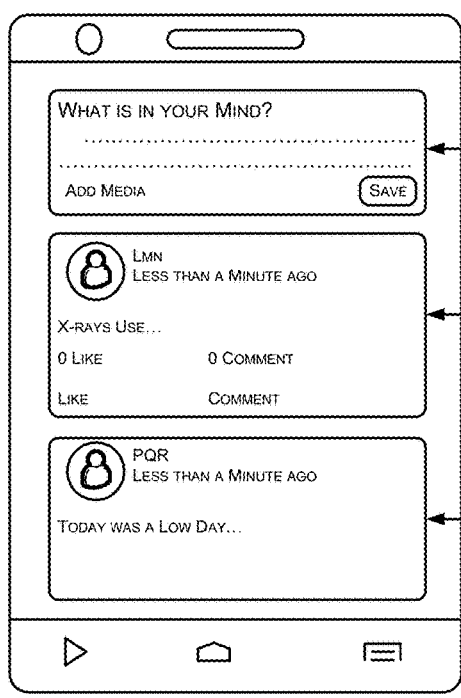
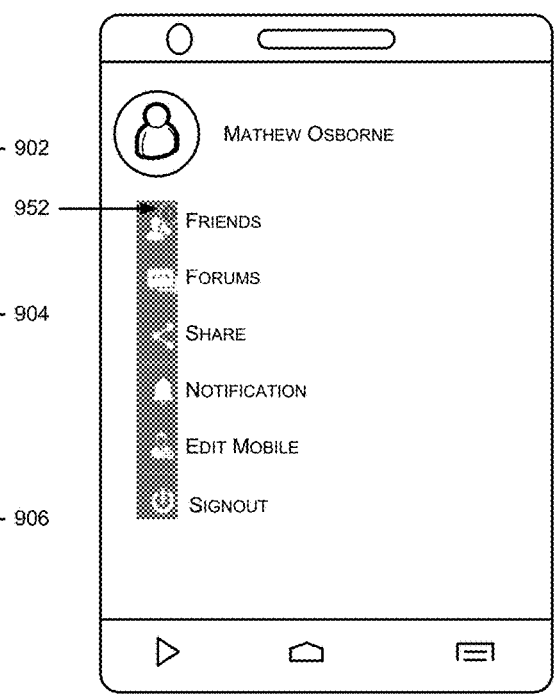
FIG. 9A                    FIG. 9B

| REPOSITORY | FORUMS | CONNECTION | MESSAGES | NOTIFICATIONS | 🔍 | MATTHEW |
|---|---|---|---|---|---|---|

REPOSITORY

> 📄 EMERGENCY
> 4 FILE(S)

> 📄 XRAY-REPOR...
> 2 FILE(S)

> 📄 PERSONAL-REPOR...
> 2 FILE(S)

📄 XRAY-NEW.J...

📄 XRAY-LEG.J...

DRAG AND DROP ePHRs HERE 2.3 MB/100MB

ALLOWED FILE TYPES: JPG, PNG, MP-4, PDF AND DOCS

| NAME | SIZE 1052 | FILE TYPE 1054 | UPLOADED DATE 1056 |
|---|---|---|---|
| ☐ EMERGENCY | | | 2016-05-12 |
| ☐ XRAY-REPOR... | | | 2016-05-12 |
| ☐ PERSONAL-REPOR... | 152914 | JPG | 2016-05-12 |
| ☐ XRAY-NEW.J... | 279213 | JPG | 2016-04-11 |
| ☐ XRAY-LEG.J... | | | 2016-03-21 |

CREATE FOLDER

SHARE HISTORY

FIG. 10B

DEPRESSION

| | REPOSITORY | FORUMS | CONNECTION | MESSAGES | NOTIFICATIONS | 🔍 | MATTHEW 👤 ▶ |

SHOW ME
● ALL FORUM
○ I AM LOOKING FOR 1102 🔍
○ ONLY THE ONES THAT MATCH MY METRO AREAS
○ FORUMS I HAVE ALREADY SUBSCRIBED TO

WHERE
● ANY WHERE
○ LOCAL CITY

DISCUSSION THREADS MATCHING YOUR INTREST

ANXIETY DISORDER
IN: US MEDICAL
0 REPLIES

ANXIETY AND ...
IN: HJKL SCHOOL
4 REPLIES

SNOW WEATHER
IN: JKL PROBLEM
0 REPLIES

WHAT AGAIN
IN: JKL PROBLEM
0 REPLIES

QWERT
IN: JKL PROBLEM
0 REPLIES

1104 🔍

| FORUM 1108 | TOPICS 1110 | POSTS 1112 | LAST POST 1114 | KEYWORDS | |
|---|---|---|---|---|---|
| ANXIETY DISORDERS ANXIETY DISORDERS ARE......... | 10 | 30 | 2016-05-20 | CHILDREN'S HEALTH... | ☑ SUBSCRIBE 1106 |
| DEPRESSION BELOW ARE LISTED......... | 8 | 6 | 2016-05-07 | HEADACHE MEDICINE | ☑ SUBSCRIBE |

FIG. 11A

SYSTEM AND METHOD FOR ELECTRONIC COMMUNICATION

CROSS-REFERENCE TO RELATED APPLICATIONS

This application claims priority to U.S. Provisional Patent Application No. 62/336,849 filed on May 16, 2016, the complete disclosure of which, in its entirety, is herein incorporated by reference.

TECHNICAL FIELD

The embodiments herein generally relate to networking systems and devices, and more particularly relate to a communication network based system and device.

BACKGROUND

The healthcare industry has seen tremendous growth in the past few years, especially with the advent of new medical indications, preventive health checkups, and advanced medical treatments. As of result of this, the number of health records generated is significant and warrants appropriate management and security due to sensitivity and confidentiality of the data involved therein.

As defined in the industry (see www.healthit.gov), a personal health record (PHR) is distinct from an electronic medical record (EMR) in many ways. Generally, a PHR is configured as an electronic application, which healthcare patients use to manage, organize, and maintain their respective healthcare information in a secure manner. EMRs are generally computerized versions of the paper charts that are generated when a patient visits a doctor's office, hospital, or medical clinic. While EMRs are managed and maintained by the healthcare facilities and entities themselves (e.g., hospitals, clinics, doctor offices, insurance companies, etc.), PHRs are managed and maintained by the patients. In this regard, PHRs and EMRS are distinct systems. As a patient, one may have medical records at different locations (i.e., different physician offices, hospitals, clinics, etc.) each with its own distinct EMR system that usually does not communicate with each other. This lack of sharing can lead to duplication of tests or imaging by healthcare providers who are unaware of a particular patient's previous tests and results.

SUMMARY

The embodiments herein provide a system for enabling electronic communication of a health record stored in a first user communication device with a second user communication device, the system comprising: a non-transitory storage device having embodied therein one or more routines operable to enable communication of the health record; and one or more processors coupled to the non-transitory storage device and operable to execute the one or more routines, wherein the one or more routines comprise: a user registration module, which when executed by the one or more processors, enables the first user communication device to register a computer-generated user profile, and add one or more user communication devices as electronic networked connections based on any of profile information, a medical condition of a first user using the first user communication device, a geographical location of the first user communication device, common medical practitioner(s), demographic attributes of the first user using the first user communication device, psychographic attributes of the first user using the first user communication device, a location of the first user using the first user communication device, and interests of the first user using the first user communication device; a health record upload module, which when executed by the one or more processors, enables uploading of the health record onto a central repository; and a health record sharing module, which when executed by the one or more processors, enables the first user communication device to select the second user communication device from a list of a plurality of user communication devices and share the uploaded health record with the second user communication device.

In an aspect, the second user communication device can include any of a communication device associated with a medical practitioner that the first user communication device intends to interact with, a communication device associated with a medical practitioner that the first user communication device has previously interacted with, a communication device associated with a user selected from a list of electronic connections of the first user communication device, and a communication device associated with an entity that the first user communication device elects to share the health record with. In another aspect, the health record can be uploaded by any of the first user communication device and the communication device associated with the medical practitioner that enables generation of the health record. The central repository can be configured in any of a server and a cloud.

In another aspect, the proposed system can further include an interface that enables the first user communication device to post any of an electronic comment, a digital image, a computer-generated discussion topic, an update to a computer-generated user profile, an electronic message, and an electronic reply message.

In an aspect, the uploaded health record can be stored in a defined computer folder in a computer file format that is implemented in the central repository. In another aspect, the proposed system can include a computer-enabled forum that enables electronic discussion of any of a health-related issue, medical journal, medical topic, and a medical conference. In yet another aspect, the electronic discussion can be restricted based on any of a medical condition of the first user using the first user communication device and a geographical location of the first user using the first user communication device. In another aspect, the uploaded health record can include any of a stored and shared electronic personal health record that is communicatively transmitted from the first user communication device to the second user communication device in an encrypted format.

Another embodiment provides a communication system comprising a first electronic communication device configured for transceiving electronic personal health records; a second electronic communication device communicatively linked to the first electronic communication device, wherein the second electronic communication device is configured for transceiving the electronic personal health records; a cloud-based document server communicatively linked to the first and second electronic communication devices; a file sharing platform communicatively linked to each of the cloud-based document server, the first electronic communication device, and the second electronic communication device, wherein digital files may be saved, accessed, and transferred to/from the cloud-based document server to the first and second electronic communication devices through the file sharing platform; an electronic forum communicatively linked to each of the cloud-based document server, the first electronic communication device, the second electronic communication device, and the file sharing platform, wherein the electronic forum is geographically localized based on network configurations retrieved from a global positioning system (GPS); a communication network linking the cloud-based document server, the first electronic communication device, the second electronic communication device, the file sharing platform, and the electronic forum together; at least one computer processor operatively linked to the cloud-based document server; a first computer module running on the cloud-based document server, which when executed by the at least one computer processor, enables the first electronic communication device to register a computer-generated user profile, and add one or more other communication devices as electronic networked connections based on parameters comprising any of profile information, a medical condition, a geographical location, a medical practitioner, demographic attributes, and psychographic attributes; a second computer module running on the cloud-based document server, which when executed by the at least one computer processor, enables uploading of a digital health record onto the cloud-based document server; and a third computer module running on the cloud-based document server, which when executed by the at least one computer processor, enables the first electronic communication device to select the second electronic communication device from a list of a plurality of user communication devices and share the uploaded health record with the second electronic communication device.

In an aspect, the second electronic communication device can include any of a communication device associated with a medical practitioner that the first electronic communication device intends to interact with, a communication device associated with a medical practitioner that the first electronic communication device has previously interacted with, a communication device associated with a user selected from a list of electronic connections of the first electronic communication device, and a communication device associated with an entity that the first electronic communication device elects to share the digital health record with. In yet another aspect, the digital health record can be uploaded to the cloud-based document server by any of the first electronic communication device and the communication device associated with the medical practitioner that enables generation of the digital health record.

In yet another aspect, the proposed system can further include a web-based computer interface that enables the first electronic communication device to post to any of the file sharing platform and the electronic forum any of an electronic comment, a digital image, a computer-generated discussion topic, an update to a computer-generated user profile, an electronic message, and an electronic reply message. In an aspect, the uploaded digital health record can be stored in the cloud-based document server in a defined computer folder in a computer file format that is implemented in the cloud-based document server. In another aspect, the electronic forum can enable electronic discussion of any of a health-related issue, medical journal, medical topic, and a medical conference, wherein the electronic discussion can be restricted based on any of a medical condition of a first user using the first electronic communication device and a geographical location of the first user using the first electronic communication device. In an aspect, the uploaded digital health record can include any of a stored and shared electronic digital health record that can be communicatively transmitted from the first electronic communication device to the second electronic communication device in an encrypted format.

Another embodiment provides a communication system comprising a first mobile communication device configured for transceiving electronic personal health records; a second mobile communication device communicatively linked to the first mobile communication device, wherein the second mobile communication device is configured for transceiving the electronic personal health records; an electronic document repository communicatively linked to the first and second mobile communication devices; a file sharing platform communicatively linked to each of the electronic document repository, the first mobile communication device, and the second mobile communication device, wherein digital files may be saved, accessed, and transferred to/from the electronic document repository to the first and second mobile communication devices through the file sharing platform; an electronic forum communicatively linked to each of the electronic document repository, the first mobile communication device, the second mobile communication device, and the file sharing platform, wherein the electronic forum is geographically localized based on network configurations retrieved from a global positioning system (GPS); a communication network linking the electronic document repository, the first mobile communication device, the second mobile communication device, the file sharing platform, and the electronic forum together; at least one computer processor operatively linked to the electronic document repository; a user registration module, which when executed by the at least one computer processor, enables the first mobile communication device to register a computer-generated user profile, and add one or more other communication devices as electronic networked connections based on parameters comprising any of profile information, a medical condition, a geographical location, a medical practitioner, demographic attributes, and psychographic attributes; a health record upload module, which when executed by the at least one computer processor, enables uploading of a digital health record onto the electronic document repository; and a health record sharing module, which when executed by the at least one computer processor, enables the first mobile communication device to select the second mobile communication device from a list of a plurality of user communication devices and share the uploaded health record with the second mobile communication device, wherein the uploaded digital health record comprises any of a stored and shared electronic digital health record that is communicatively transmitted from the first mobile communication device to the second mobile communication device in an encrypted format.

In an aspect, the system can include a web-based computer interface that enables the first mobile communication device to post to any of the file sharing platform and the electronic forum any of an electronic comment, a digital image, a computer-generated discussion topic, an update to a computer-generated user profile, an electronic message, and an electronic reply message, wherein the uploaded digital health record can be stored in the electronic document repository in a defined computer folder in a computer file format that is implemented in the electronic document repository.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 8B illustrates a second webpage for interfacing with the system according to an embodiment herein.

FIG. 9A illustrates an add/update status interface according to an embodiment herein.

FIG. 9B illustrates a central interface of the system provided by the embodiments herein.

FIG. 10B illustrates a list view of the repository according to an embodiment herein.

FIGS. 11A to 11E illustrate various interfaces related to forums that may be enabled by the system provided by the embodiments herein.

DETAILED DESCRIPTION

Figure 1:
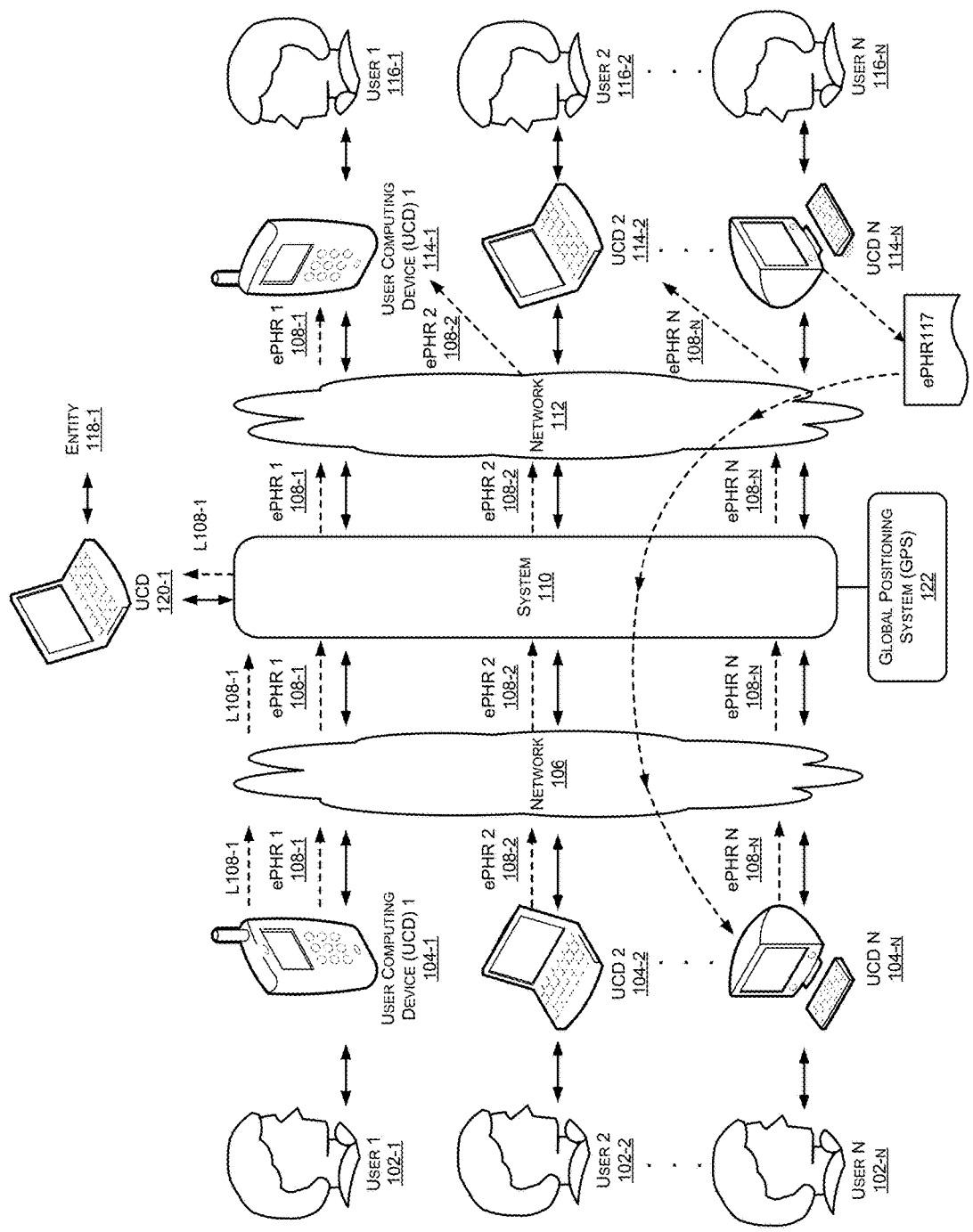
FIG. 1 illustrates an overall architecture diagram of the system provided by the embodiments herein.

In accordance with the embodiments herein, there is provided a system and a method for network based sharing and management of health records, as elaborated hereunder using an exemplary embodiment. The embodiments herein do not limit the scope of the disclosure. The description relates purely to the exemplary embodiments and its suggested applications.

The various modules described by the examples herein and illustrated in the figures may be embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which may include a plurality of transistors and other supporting devices and circuit elements. The modules that are configured with electronic circuits process computer logic instructions that provide digital and/or analog signals for performing various functions as described herein. The various functions may be embodied and physically saved as any of data structures, data paths, data objects, data object models, object files, and database components. For example, the data objects may be configured as a digital packet of structured data. The data structures may be configured as any of an array, tuple, map, union, variant, set, graph, tree, node, and an object, which may be stored and retrieved by computer memory and may be managed by processors, compilers, and other computer hardware components. The data paths may be configured as part of a computer central processing unit (CPU) that performs operations and calculations as instructed by the computer logic instructions. The data paths may include digital electronic circuits, multipliers, registers, and buses that perform data processing operations and arithmetic operations such as Add, Subtract, etc., bitwise logical operations such as AND, OR, XOR, etc., bit shift operations such as arithmetic, logical, rotate, etc., complex operations such as using single clock calculations, sequential calculations, iterative calculations, etc. The data objects may be configured as physical locations in computer memory and may be a variable, a data structure, or a function. In the examples configured as relational databases such as Oracle® relational databases, the data objects may be configured as a table or column. Other configurations include specialized objects, distributed objects, object oriented programming objects, and semantic web objects, for example. The data object models may be configured as an application programming interface for creating HyperText Markup Language (HTML) and Extensible Markup Language (XML) electronic documents. The models may be configured as any of a tree, graph, container, list, map, queue, set, stack, and variations thereof. The data object files may be created by compilers and assemblers and contain generated binary code and data for a source file. The database components may include any of tables, indexes, views, stored procedures, and triggers.

The system provided by the embodiments herein enables a secure health records repository to enable its members/users/patients effectively and economically manage, update, and communicate the very critical record keeping and retrieval aspects of their health. The system provided by the embodiments herein may enable its members to connect with other members in a very quick one-click manner, upload and share digital versions such as scanned copies of their personal health records (such copies hereinafter referred to as Electronic personal health records or ePHRs), post status updates, exchange messages with their friends (interchangeably termed as connections herein), and sort the uploaded ePHRs in different suitably named/folders so as to enable their quick retrieval when required including a "Emergency" folder to keep all records useful in an emergency; and have access to an interface (or a plurality of interfaces) to discuss health-related issues, latest medical advances, pros and cons of a particular treatment, opinions about medical practitioners, with a degree of anonymity as per their choice, as described further below.

In another aspect, the system may enable a health portal to its members providing them a secure and convenient access anytime (24×7) to their electronic personal health records in a platform-independent manner so that the records are retrievable and readable by anyone so authorized, irrespective of the computer system and operating system they might be using. Data being held in and transferred using the system may utilize encryption methods and protocols to ensure security and confidentiality during storage as well as transmission. The system provided by the embodiments herein may ensure that the storage and transmission of ePHRs complies with local legislations concerning medical data privacy and security, such as the U.S. HIPAA (Health Insurance Portability and Accountability Act of 1996) laws.

In exemplary embodiments, the system may allow patients (interchangeably termed as members and users herein) to upload photos and records pertaining to their medical history, diagnosis, symptoms, appearance, injuries, wounds and the like, wherein such documents, after uploading, being collectively referred to as personal health records or electronic personal health records (ePHRs). An ePHR may be tagged by at least one parameter, and may be easily retrievable by using any of such parameters as described further below. In exemplary embodiments, such parameters may include body anatomy (for example, dental records, chest X-Rays, abdominal records, kidney records, etc.), medical procedures performed (such as blood test, urine test, X-ray, ECG, chemotherapy, etc.), disease (diabetes, skin allergy, heart angina, etc.), and doctors/hospitals visited, etc. All such parameters may visually be represented as folders onto a display device of the user's computing device, as described further and the same ePHR may be accessible from more than one folders depending upon how it is tagged. For example, a report on a chemotherapy procedure performed on a cancer patient may be accessible from the patient's disease folder (cancer), procedure folder (chemotherapy), and the hospital folder, depending upon how the report has been tagged. For lighter storage, all ePHRs of a patient/user may be stored in a repository allotted by the system provided by the embodiments herein to him/her and various folders may carry pointers based upon tagging performed to the document according to which the ePHRs may be retrievable form a plurality of folders.

In an aspect, the system provided by the embodiments herein may provide certain default folders to a patient upon his/her registration while others may be created by the user in the manner described above. For example, an 'Emergency" folder may be provided by default to a user in which all ePHRs tagged "Emergency" by the user may be reflected, for use in emergency situations as described further below.

In another aspect, the system may enable a patient (that may be termed as a first user herein) to create a profile for himself/herself that may be visually represented as a webpage, and also show any of his/her ePHRs/folders as per his/her wishes onto this webpage and share any of his/her ePHRs/folders with another user authorized by him/her. The "another user" (interchangeably termed as second user) may include any of a medical practitioner that the first user intends to consult, a medical practitioner that the first user has previously consulted, a user selected from a list of connections of the first user, or an entity that the first user wishes to share the health record with, the entity being anybody not registered with the system provided by the embodiments herein.

In yet another aspect, the user may share an ePHR/folder with an entity (or a plurality of entities) not registered with the system. In an exemplary embodiment, such an entity may be sent a time bound link on its computing device, upon appropriate action by a user using the system provided by the embodiments herein. Clicking on the link may enable the entity to view/download the ePHR/folder on his/her computing device. In this manner, the system may enable a user to, for example, share all his/her prior dental records with a new dentist so that the new dentist already has full information regarding the patient's dental history before he commences treatment.

In an aspect, the system may enable a user to share his/her experience, views, and opinions with other users and likewise for all users, whereby various users may learn and gain from such views, experiences, and opinions of other users. In one aspect, an interface may be enabled via a webpage accessible/viewable to all users of the system so permitted by the user, wherein the user may comment with his/her updates, views, opinions, experiences, etc. and other users may view/receive such data or their notifications on their respective computing devices depending upon the privacy settings chosen by the user for each such data item. In alternate exemplary embodiments, such privacy settings may be "only friends", "friends of friends", and "public" wherein friends are other users directly connected to the user (i.e., user's "connections", as described above).

In another aspect, another means enabled by the system provided to a user to share his/her experience, views, and opinions with other users and likewise for all users, whereby various users may learn and gain from experience of other users, may include various forums. The system may enable a user to create a forum and invite other users to participate, as well as join forums created by others based upon invitations received by them. In yet another aspect, a forum may be a "public" forum that any user may join without requiring an invitation from the creator/user of the forum. The system may enable a user to create a forum on any relevant subject such as disease, anatomy, treatment, physiological and psychological aspects of a disease, experiences with various medical institutions or doctors, etc. A user who is also a medical specialist may, for example, create a forum on his/her medical specialty, wherein other users suffering from the malady he/she is specializing in may join and ask his/her advice. Even other medical specialists of the same malady/ disease may also join in thereby providing different opinions to forum members.

In an aspect, a forum may be searchable based on one or more parameters by a member user via appropriate interfaces provided on the user's computing device. Such parameters may include, for example, any of a geographical location of a user, the time since he/she has been a member of the forum, the participation level of the user (that may be evidenced by number of comments/posts made by the user during a pre-determined period of time), and the expertise of the user (that may be determined based on the number of other users agreeing to the user's comments, such number being determined, for example by a suitable algorithm implemented on each comment). A user may connect, for example, with other users in the same locale as himself/ herself and having the same medical problems so as to gain from each other's experience. The user may exercise full control over his/her ePHRs in aspects of such ePHRs' visibility and sharing. Likewise, the user may exercise full control over his/her profile's visibility to other users. For example, a user may decide to make his/her name and location visible in one forum but not in another. Likewise, he/she may decide to keep one of his/her ePHR hidden while others may be visible to his/her direct connections only.

In another aspect, the system provided by the embodiments herein provides for a networking device that may be configured to link to a website where content as well as control over dissemination and viewing of the content is exercised by its creators. The networking device maybe configured in, or be operatively connected to any computing device, including mobile devices using mobile applications that may be downloaded on the mobile devices. The embodiments herein provide every user a repository that may be in a cloud or a server and accessed by the user using an interface such as the website and subsequent interfaces provided within the website. The user may store his/her health records in an electronic form (referred to as Electronic personal health records herein) in the repository and such records then may be shared with other users via the website, under control of their "owner" (such owner being the user who provides the records to the repository or to whom the records pertain). Various means of sharing such records with varying degree of privacy and security may be provided and include, but are not limited to, private message to other users, posting an ePHR or its link in public forums, transmitting via E-mail to users/non-users etc. The users as well as non-users may include friends, physicians, family, hospitals, healthcare systems, insurance companies, and anybody else, including social networks the user may be using. All ePHRs may be stored and shared in a secured and HIPAA complaint platform.

In yet another aspect, the system may enable all its users with appropriate interfaces for sharing their ePHRs as well as experiences, comments, views, opinions, etc. One such interface may include forums wherein users may search for messages posted by other users using various search criteria such as disease, location, treatment, medications, side effects, psychological issues, rehabilitation, end of life (EOL) treatment options, etc. Search criteria may be enabled by appropriate search forms that may be provided as templates by the embodiments herein, such templates being further customizable by users to their unique requirements.

In an exemplary embodiment, the system may be configured in kiosks that may be installed at suitable places such as hospital lobbies, doctor's waiting rooms, pharmacies, etc. Using such kiosks, a user may access the system provided by the embodiments herein and retrieve/share his/her ePHRs as required.

In another aspect, the system may enable medical practitioners and hospitals to build virtual "patient villages" of users interested in their services (such users being past patients as well as prospective patients, for example) and send such users updates on their services, breakthrough medical studies and research being performed by them, innovative treatment options, special time bound discounted rates for procedures being performed regularly by them, etc. In this manner, the visibility of such hospitals and doctors increases and also helps them retain their patients and get new ones.

These and other aspects of the embodiments herein will be better appreciated and understood when considered in conjunction with the following description and the accompanying drawings. It should be understood however that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

FIG. 1 illustrates an overall architecture diagram of a system 110 and describes its overall functioning, in accordance with an embodiment herein. In an aspect, the system 110 may be operatively configured such that it is accessible using any Internet enabled computing device. System 110 may be, for instance, configured with a mobile application that may be downloaded on any mobile device to enable access to the website and all its features, suitably adapted to be operated via the mobile device. Another exemplary configuration of the system 110 may also be performed as a website that is hosted on a server and is operatively coupled to a central database such as the cloud. All communications amongst different users of the system 110 may take place through respective computing devices of corresponding users and suitably configured communication networks 106, 112.

In another aspect, using a computing device 104-1, 104-2, . . . 104-N, a user 102-1, 102-2, . . . 102-N of the system 110 may provide his/her personal health records in an electronic format such as ePHRs 108-1, 108-2, . . . 108-N to the system 110 via a suitable network 106. The system 110 may further store such records in a secure storage space (interchangeably termed as repository) provided by the system 110 to the user 102-1, 102-2, . . . 102-N, and likewise, to every user. Each user 102-1, 102-2, . . . 102-N may have his/her own fully secure repository that may be accessible only to him/her and to other users 116-1, 116-2, . . . 116-N authorized by him/her.

In yet another aspect, user 102-1, 102-2, . . . 102-N may retrieve ePHRs provided by him/her to system 110 using his/her computing device 104-1, 104-2, . . . 104-N and may share one or more of his/her ePHRs 108-1, 108-2, . . . 108-N with other users 116-1, 116-2, . . . 116-N who, in turn, may be using the system 110 with their computing devices 114-1, 114-2, . . . 114-N. The other users 116-1, 116-2, . . . 116-N may in turn provide the user 102-1, 102-2, . . . 102-N advice and suggestions through their computing devices 104-1, 104-2, . . . 104-N, such advice and suggestions etc. being retrievable by the user 102-1, 102-2, . . . 102-N on his/her computing device 104-1, 104-2, . . . 104-N.

For example, user 102-1 may share one of his/her ePHRs (e.g., ePHR 108-1) uploaded by him/her to the system 110 with another user 116-1, whereby the ePHR 108-1 may be retrieved and presented on user 116-1's computing device 114-1, and user 102-2 may also share one of his/her ePHR (ePHR 108-2) uploaded by him/her to system 110 with user 116-1. Similarly, user 102-N may share one of his/her ePHR (ePHR 108-N) with user 116-2. A user can share ePHRs 108-1, 108-2, . . . 108-N uploaded by him/her to system 110 with any other user entirely at his/her option. Such sharing may be enabled by allowing user 102-1, 102-2, . . . 102-N to upload his/her ePHRs 108-1, 108-2, . . . 108-N on a cloud/server, and sharing one or more desired/selected ePHRs 108-1, 108-2, . . . 108-N with other users 116-1, 116-2, . . . 116-N registered with the system 110. If configured in the system 110, sharing may also be performed with users 116-1, 116-2, . . . 116-N such as medical practitioners/doctors who are not registered with the system 110. In another aspect, sharing of health records may not be necessarily performed by the patient/user to whom the records pertain, but may also be performed by the medical practitioner/hospital that was involved in the generation of the records; e.g., by a diagnostics center or a medical institution.

In a similar manner, system 110 may enable a plurality of users 102-1, 102-2, . . . 102-N, each using a computing device 104-1, 104-2, . . . 104-N (such as a laptop, desktop PC, mobile phone, smart phone, PDA, smart watch, tablet PC, or any other computing device) to access system 110 and upload their ePHRs 108-1, 108-2, . . . 108-N and share their ePHRs 108-1, 108-2, . . . 108-N with any other user 102-1, 102-2, . . . 102-N or 116-1, 116-2, . . . 116-N.

A plurality of means may be provided as further elaborated to facilitate sharing of ePHRs 108-1, 108-2, . . . 108-N. A user (e.g., 102-1, for example) may form connections with other users 116-1, 116-2, . . . 116-N and further segregate such connections into groups as per his/her requirement. For example, a group of family connections may be formed. The user (e.g., 102-1, for example) may share any of his/her ePHRs 108-1, 108-2, . . . 108-N with individual connections or all connections in a group.

In another aspect, system 110 may enable a user (interchangeably termed as first user) to authorize another user (interchangeably termed as a second user) to upload first user's ePHR (that may have been generated by the second user) to the first user's repository and thereafter the first user may share such ePHR in same manner as above. Such authorization may be provided to the second user in any manner chosen by the first user. For example, it may be limited by time or by a link sent to the second user by the first user that the first user may make non-functional when he wants.

In an exemplary embodiment, system 110 may enable medical practitioners to register and upload ePHRs of their patients, such ePHRs being generated by the medical practitioners during their treatment of their patients and the patients may further download such ePHRs and share them with others as well, in a similar manner as described above.

In an exemplary embodiment, a patient (first user) may send an Internet or SMS invitation to his/her medical practitioner (presently a potential user) to register with the system 110. The invitation may carry a unique link that the medical practitioner may use to register with system 110 in a single click. After such registration, the medical practitioner may be considered as any other user with access to similar functions.

In another exemplary embodiment, user 102-N may send an invitation as described above to his/her medical practitioner and the medical practitioner may become user 116-N, using his/her computing device 114-N configured to connect to the system 110 via network 112. In a similar manner, other users 116-1, 116-2 may also become members using their respective computing devices 114-1 and 114-2, respectively. Further, user 102-N may authorize user/medical practitioner 116-N through their respective computing devices 104-N and 114-N, respectively, to upload an ePHR 117 generated by user/medical practitioner 116-N for user 102-N in a repository of users 102-N and 116-N may be enabled by the system 110 to perform accordingly, using his/her computing device 114-N. User 102-N may receive ePHR 117 on his/her computing device 104-N and, in turn, share the ePHR 117 with other users 102-1, 102-2, 116-1, 116-2, etc. via their respective computing devices 104-1, 104-2, 114-1, 114-2, etc.

In an aspect, a user 102-1, 102-2, . . . 102-N may also form forums or join existing ones wherein he/she may share any of his/her ePHRs 108-1, 108-2, . . . 108-N as well as peruse others' available ePHRs 108-1, 108-2, . . . 108-N and have various discussions. Users 102-1, 102-2, . . . 102-N may have various health-related discussions and offer each other advise, suggestions, and support.

In yet another aspect, a user 102-1 may share an ePHR/folder with an entity 118-1 (or a plurality of entities) not registered with the system 110, and such an entity may include social networks that the user 102-1 is member of. In an exemplary embodiment, user 102-1 may associate ePHR 108-1 with a time bound link/URL illustrated in FIG. 1 as L108-1 that the user 102-1 may also associate with an e-mail address of entity 118-1 using an interface enabled by system 110, and send the ePHR link L108-1 to system 110. System 110 may, in turn, automatically forward link L108-1 to an e-mail inbox of entity 118-1. Entity 118-1 may receive link L108-1 on its computing device 120-1 and click on the link L108-1 to retrieve ePHR 108-1 from system 110. In another exemplary embodiment, link L108-1 may be sent by SMS or any other suitable electronic text communication method or system.

In an aspect, system 110 can be operatively coupled with a GPS 122 to enable localized searching for one or more users.

In an aspect, it should be appreciated that described types of documents (such as ePHRs) that may be shared (e.g., file format) and utilized in the system are only exemplary in nature and such documents could be of any type or file format. For instance, the document can be a video file or an audio file or an image or can simply be a text file. Therefore, any type of file can be incorporated in the proposed system and is well within the scope of the present invention.

Figure 2:
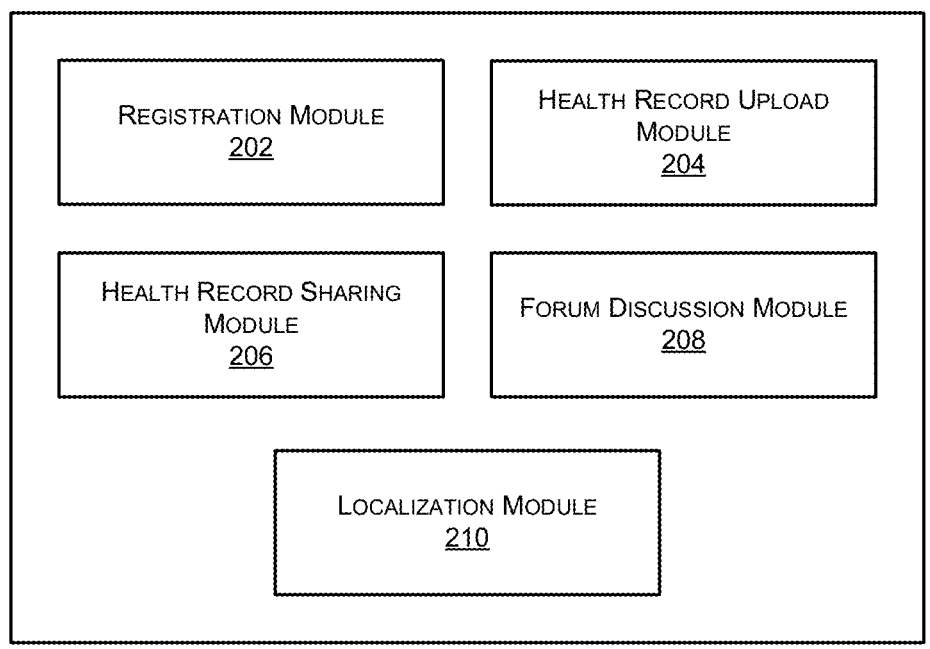
FIG. 2 illustrates various main modules of the system provided by the embodiments herein.

FIG. 2, with reference to FIG. 1, illustrates various modules 202, 204, 206 of the system 110. In an aspect, system 110 may include a user registration module 202, a health record upload module 204, and a health record sharing module 206. In another aspect, modules 202, 204, 206 may be operatively configured with appropriate user interfaces, repositories/databases, and APIs as required.

In an aspect, registration module 202 may enable registration of a person/user 102-1, 102-2, . . . 102-N. System 110 may adapt registration interfaces according to the type of computing device 104-1, 104-2, . . . 104-N a person is using. For example, for a personal computer with a large display area all aspects of registration may be embodied in a single form but for a mobile device with smaller display area, various aspects of registration may be spread over multiple forms/screens.

In an aspect, the registration module 202 may receive, from a potential user, his/her basic information such as name, gender, user ID, password, location, etc. as well as other details such as his/her medical condition, photograph, summary of prior medical history, treatments taken, health records that the user 102-1, 102-2, . . . 102-N possesses, medications taken, etc. to build an appropriate user profile for further use as required. Drop-down menu options as well as free form fields may be provided in the registration module 202 to build the user profile. After registration, a user 102-1, 102-2, . . . 102-N may login using his/her user ID and password on any Internet-enabled computing device 104-1, 104-2, . . . 104-N into a website of the system 110.

In an aspect, module 202 may enable the user 102-1, 102-2, . . . 102-N to add one or more users 116-1, 116-2, . . . 116-N as his/her connections based on any or a combination of profile information, medical condition of the user 102-1, 102-2, . . . 102-N, medical treatment that the user 102-1, 102-2, . . . 102-N has undergone, geographical location of the user 102-1, 102-2, . . . 102-N, common medical practitioner(s), demographic attributes of the user 102-1, 102-2, . . . 102-N, psychographic attributes of the user 102-1, 102-2, . . . 102-N, location of the user 102-1, 102-2, . . . 102-N, and interests of the user 102-1, 102-2, . . . 102-N. Module 202 may provide all relevant user registration data, including details of his/her profile and all activities (such as connections made by him/her) of the user 102-1, 102-2, . . . 102-N to an appropriate repository/database for future retrieval, update, and use as required.

In an aspect, the health record upload module 204 of system 110 may enable a user 102-1, 102-2, . . . 102-N to upload scanned and/or digital copies of his/her health records (e.g., ePHRs 108-1, 108-2, . . . 108-N) into his/her allotted storage space/repository enabled by system 110 for future retrieval as required. Further, during the process of scanning, module 204 may enable the user 102-1, 102-2, . . . 102-N to provide tags to the ePHRs 108-1, 108-1, . . . 108-N on the basis of which the ePHR 108-1, 108-2, . . . 108-N may be indexed and put into appropriate folders. For example, an X Ray report "A" may be tagged as an X-Ray and system 110 may automatically create a folder entitled "X-Ray" and place a pointer in the folder pointing towards ePHR "A". Further X-ray reports, if similarly tagged, may similarly be handled. In another aspect, a user 102-1, 102-2, . . . 102-N may create folders and manually move the uploaded ePHRs 108-1, 108-2, . . . 108-N into such folders, with the system 110 automatically creating pointers as described above. An ePHR 108-1, 108-2, . . . 108-N may be provided with multiple tags and accordingly, the ePHR 108-1, 108-2, . . . 108-N may be retrievable using pointers provided in corresponding multiple folders. In this manner, an ePHR 108-1, 108-2, . . . 108-N stored in the repository of a user 102-1, 102-2, . . . 102-N may be retrievable from multiple folders or using multiple criteria thereby reducing computer space requirements. In another aspect, folders may be created by the user 102-1, 102-2, . . . 102-N and an ePHR computerized file stored therein by manual means, such as drag and drop, copy/paste, etc., without any such tagging.

In another exemplary embodiment, module 204 may automatically retain uploaded ePHRs 108-1, 108-2, . . . 108-N in defined folders by means of various file formats that may be implemented in the repository. For example, an ePHR, which may be in a pdf format, for example, may automatically be filed in a folder named "PDF documents", and another ePHR in a bmp format may automatically be filed in a folder named "BMP documents".

In an aspect, module 204 may encrypt an ePHR 108-1, 108-2, . . . 108-N while uploading it to the repository of a user 102-1, 102-2, . . . 102-N and provide appropriate decryption algorithms when the user 102-1, 102-2, . . . 102-N is sharing the ePHR 108-1, 108-2, . . . 108-N with another user 116-1, 116-2, . . . 116-N so that the other user 116-1, 116-2, . . . 116-N may decrypt the ePHR 108-1, 108-2, . . . 108-N upon receipt, while all transmissions of the ePHR 108-1, 108-2, . . . 108-N over various networks 106, 112 take place in encrypted formats.

As also mentioned above, ePHRs 108-1, 108-2, . . . 108-N may not necessarily be uploaded by user/patient 102-1, 102-2, . . . 102-N to whom the records pertain and may also be uploaded by a medical institution/hospital/medical professional that was responsible for generation of the health records. Any other stakeholder such as a family member can also upload the desired health records. It may also be possible that only a certain part of the health records is made available while others are hidden.

In an aspect, health record sharing module 206 of system 110 may enable a user 102-1, 102-2, . . . 102-N (interchangeably termed as first user herein) to share an ePHR 108-1, 108-2, . . . 108-N uploaded by him/her with any other user 116-1, 116-2, . . . 116-N (interchangeably termed as second user herein) of the system 110.

In an aspect, module 206 may enable the first user to form a list of users or likewise, a plurality of lists of users that he/she may wish to share his/her ePHR 108-1, 108-2, . . . 108-N with, such lists being interchangeably termed as lists of connections. In an exemplary embodiment, the user 102-1, 102-2, . . . 102-N may search the user's database of system 110 to identify medical practitioners dealing in diabetes and may form a list of medical practitioners for diabetes accordingly. Alternatively, the user 102-1, 102-2, . . . 102-N may send an invitation to his/her friends/family to register with the system 110, and the system 110 may automatically create a list of his/her friends/family as and when such friends/family register with the system 110. System 110 may recommend other users 116-1, 116-2, . . . 116-N to the first user to connect with, based upon various algorithms that analyze interactions of the first user as well as other users 116-1, 116-2, . . . 116-N. Depending upon permissions granted by a second user, the first user may add the second user to one of his/her list of connections, or only upon receiving an approval from the second user to perform such an addition.

In an aspect, module 206 may provide a plurality of means to the first user to share his/her ePHR 108-1, 108-2, . . . 108-N by providing user interfaces, search interfaces, etc. to the first user. Such sharing may be enabled by a plurality of means. For example, the first user may e-mail the ePHR 108-1, 108-2, . . . 108-N to the second user, or the first user may send a pointer to the ePHR 108-1, 108-2, . . . 108-N (e.g., a hyperlink, for example) to the second user by SMS. The second user may use the link to view and/or download the ePHR 108-1, 108-2, . . . 108-N as per permissions granted by the first user. In yet another exemplary embodiment, the first user may provide the hyperlink in a forum discussion. Other members of the forum may use the hyperlink to view the ePHR 108-1, 108-2, . . . 108-N. In yet another exemplary embodiment, the first user may select one or more second users from a list of connections of the first user. In another exemplary embodiment, the second user may be searchable by his/her name or by various data provided by him/her in his/her profile. For example, the first user may search for medical practitioners specializing in treatment of diabetes, may further narrow down the search to those medical practitioners who are within 10 miles of his/her present location, and send his/her latest sugar report ePHR to all such medical practitioners. It would be appreciated that although only three functional modules have been mentioned in FIG. 2 any other number of modules may be configured in view of the functional embodiments of the system 110. For example, it is possible to configure a forum discussion module 208 that enables discussion on multiple topics, medical indications, treatments, medical professional reviews, among other parameters on a forum/wall/interface between a plurality of registered users. It is also possible to configure a localization module 210 that enables users to search for friends/communities/groups and also for medical practitioners within their defined vicinity and accordingly undertake discussions, reviews (of hospitals or doctors, for instance), and appointments from amongst filtered results.

In an aspect, module 206 may enable the first user to share any of his/her ePHRs 108-1, 108-2, . . . 108-N with non-users of the system 110 as well; including the first user's other social networks such as Facebook™, Twitter™, and LinkedIn™, etc. Such non-users and external social networks may include the entity/entities 118-1.

In this manner, module 206 may enable the first user to select the second user from a list of plurality of users and share the uploaded health record (ePHR 108-1, 108-2, . . . 108-N) with the second user, wherein the second user may be any or a combination of a medical practitioner that the first user intends to consult, a medical practitioner that the first user has previously consulted, a user selected from a list of connections of the first user, and an entity 118-1 with which the first user wishes to share the health record (ePHR 108-1, 108-2, . . . 108-N). In an aspect, module 206 may enable the first user to withdraw sharing of an ePHR 108-1, 108-2, . . . 108-N from the second user. Upon such withdrawal, any links, etc. that may have been sent by the first user to the second user to enable sharing of the ePHR 108-1, 108-2, . . . 108-N may be made non-functional.

Figure 3A:
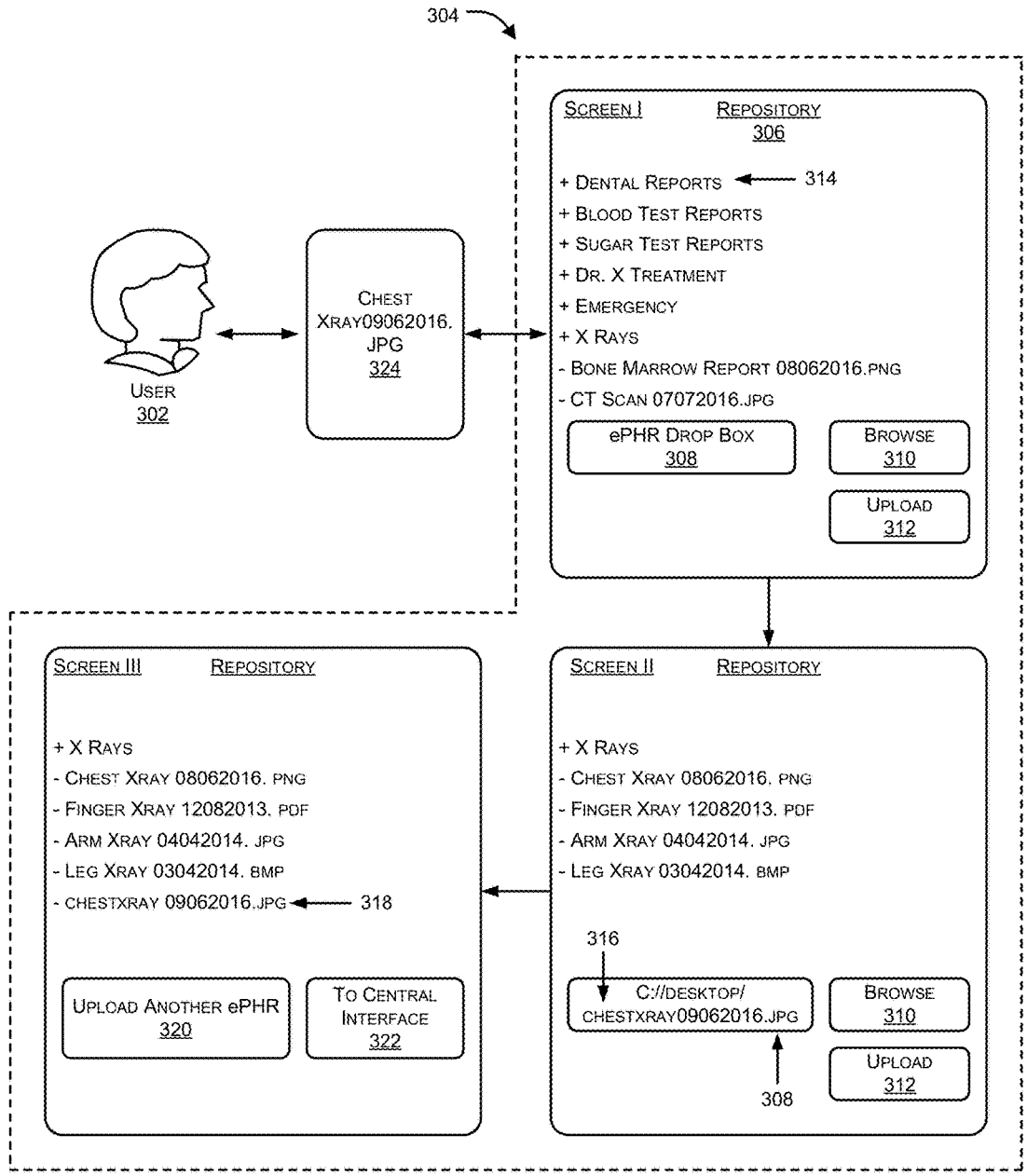
FIG. 3A is a first schematic diagram illustrating how a health record may be uploaded, stored and further shared using the system provided by the embodiments herein
Figure 3B:
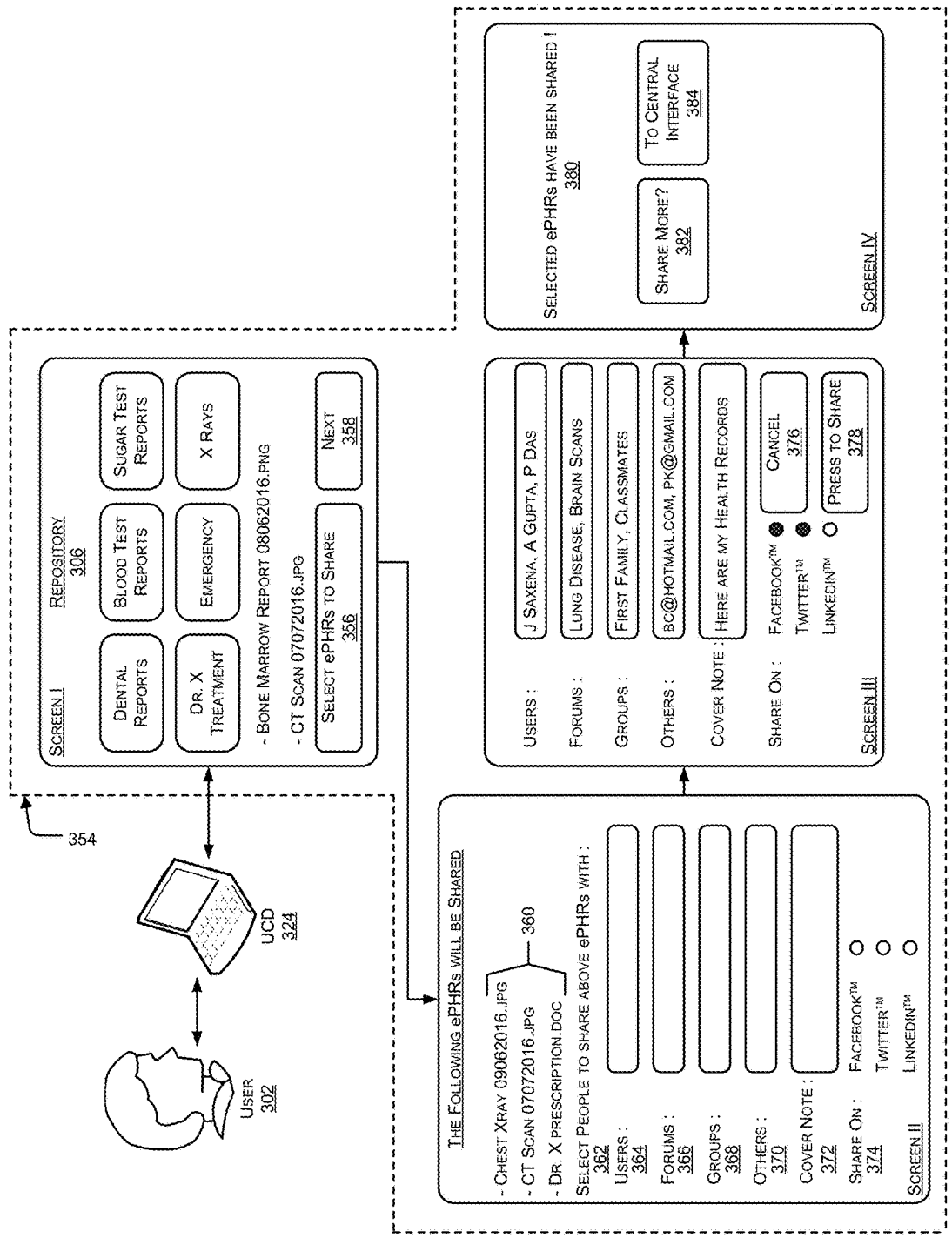
FIG. 3B is a second schematic diagram illustrating how a health record may be uploaded, stored and further shared using the system provided by the embodiments herein.

FIGS. 3A and 3B, with reference to FIGS. 1 and 2, illustrate how a health record (ePHR 108-1, 108-2, . . . 108-N) may be uploaded, stored, and shared using system 110, in accordance with exemplary embodiments herein. As illustrated in FIG. 3A, a user 302 may desire to upload a scanned copy of his/her health record (ePHR 108-1, 108-2, . . . 108-N) of his/her chest X-ray shown as CHESTXRAY08062016 that may presently be in his/her computing device 324. Using system 110 and computing device 324, user 302 may access his/her ePHR repository 306 and an upload interface 304 showing repository 306 may be displayed on his/her computing device 324. Interface 304 may initially display Screen I to the user 302, as shown. The repository 306 may already have folders with files (such as digital files containing ePHRs 108-1, 108-2, . . . 108-N) therein and some ePHRs 108-1, 108-2, . . . 108-N may be stored in the repository root itself, without being put in any folders. In an exemplary embodiment shown, the folders presently existing in repository 306 may be those for dental reports, blood test reports, sugar test reports, Dr. X treatment, emergency, and X-rays. as an example, bone marrow report 08062016.png and CT Scan 07072016.jpg may presently be lying in the root of repository 306. Each folder may have an icon that may be configured as a sign + as indicated at field 314 that user 302 can click to expand the folder and show further files and folders therein. It can be readily appreciated that folders and ePHRs 108-1, 108-2, . . . 108-N may be named as desired by the user 302.

System 110 may provide a default folder that may be named "Emergency" as shown. A user 302 may store all his/her health records (ePHR 108-1, 108-2, . . . 108-N) that may be useful in an emergency in the Emergency folder. System 110 may make available ePHRs 108-1, 108-2, . . . 108-N in the Emergency folder to anyone suitably authorized (such as the system administrator) on the basis of the user ID only, without knowing the user password/biometric. This may be very helpful in emergency situations when the user 302 (or any other user) may not be able to use the system 110 due to being incapacitated.

In an aspect, Screen I of upload interface 304 may have an ePHR drop box 308, a browse button 310, and an upload button 312. Any ePHR 108-1, 108-2, . . . 108-N dragged and dropped into ePHR drop box 308 may automatically be uploaded into repository 306, into a folder open at the time. In another aspect, the ePHR 108-1, 108-2, . . . 108-N to be uploaded can also be selected using browse button 310. To upload ePHR CHESTXRAY09062016 into its correct folder, user 302 may click on the X Rays folder to open it and display present files contained therein. Interface 304 may display Screen II. Next, ePHR CHESTXRAY09062016 may be dragged and dropped into ePHR drop box 308. Alternatively, the ePHR CHESTXRAY09062016 may be selected on user 302's computing device 324 using browse button 310 when the full path (as shown at field 316) to the ePHR 108-1, 108-2, . . . 108-N may be shown in ePHR drop box 308. Next, upload button 312 may be pressed to start the upload process. System 110 may provide a visual indication on interface 304 once the upload is complete. Interface 304 may display Screen III on user 302's computing device 324 and the uploaded file ePHR CHESTXRAY09062016 may appear in the open folder. A plurality of ePHRs 108-1, 108-2, . . . 108-N may be uploaded in a few steps by selecting them together using browse button 310 and then using the upload button 312.

In an aspect, Screen III of interface 304 may show 'upload another ePHR' button 320 and 'to central interface' button 312. User 302 may press button 320 if he/she wishes to upload another ePHR 108-1, 108-2, . . . 108-N into his/her repository 306 using interface 304, when interface 304 may again display Screen I on user 302's computing device 324, or user 302 may press button 322 when system 110 may display on his/her computing device 324 the central interface/dashboard of the system 110 (as further described below) through which the user 302 may operate all of its functions.

FIG. 3B illustrates how a user 302 may share ePHRs 108-1, 108-2, . . . 108-N from his/her repository 306 with other users 116-1, 116-2, . . . 116-N and entities 118-1, wherein entities 118-1 may be anybody who is not a user 102-1, 102-2, . . . 102-N or 116-1, 116-2, . . . 116-N of the system 110. In an aspect, user 302 may operate system 110 using his/her computing device 324 for the purpose of sharing any ePHRs 108-1, 108-2, . . . 108-N uploaded by him/her in his/her repository 306, as described above. System 110 may present to user 302 on a display of his/her computing device 324 Screen I of sharing interface 354. Screen I may display present folders and files in repository 306 and a 'select ePHRs to share' box 356 as well as a 'next' button 358. User 302 may drag and drop, for example, ePHRs 108-1, 108-2, . . . 108-N to be shared from various folders into box 356 and then press button 358.

In another aspect, once user 302 presses button 358, share interface 354 may display on user 302's computing device 324 Screen II as shown. Screen II may show ePHRs 108-1, 108-2, . . . 108-N to be shared, as shown at field 360 and may enable user 302 to select people with which to share the selected ePHRs 108-1, 108-2, . . . 108-N, as shown at field 362. Using various fields and controls provided on Screen III, user 302 may select other users 364, forums 366, groups 368, and others 370, in addition to providing a cover note 372. User 302 may also be enabled by system 110 to share selected ePHRs 108-1, 108-2, . . . 108-N on his/her other social networks such as Facebook™, Twitter™, and LinkedIn™, etc., as illustrated at share field 374. In exemplary embodiments, user 302 may select other users 116-1, 116-2, . . . 116-N from his/her connection lists and groups and forums from groups and forums he/she may have created or may be a member of. Additionally, at the others field 370, the user 302 may provide an e-mail address of people that may not be users of system 110 but with whom user 302 may still wish to share the ePHRs 108-1, 108-2, . . . 108-N selected, and at the share field 374, the user 302 may select his/her other social networks on which he/she may wish to share the ePHRs 108-1, 108-2, . . . 108-N selected. Such non-users and social networks or any combination of these may be collectively termed as an entity (or entities) 118-1.

In yet another aspect, as the user 302 selects people to share selected ePHRs 108-1, 108-2, . . . 108-N with, share interface 354 may display on user 302's computing device 324 Screen III as shown. Screen III may show various data being provided and may have a 'cancel' button 376 and a 'press to share' button 378. In case user 302 presses button 376, system 110 may cancel the share process. If the user 302 presses button 378, system 110 may commence the share process. Upon completion of the share process, share interface 354 may display on user 302's computing device 324 Screen IV as shown. Screen IV may confirm to the user 302 that selected ePHRs 108-1, 108-2, . . . 108-N have been shared, as shown at field 380 and further provide a 'share more?' button 382 and a 'to central interface' button 384. Pressing button 382 may present to user 302 Screen I of share interface 354 so as to share more ePHRs 108-1, 108-2, . . . 108-N while pressing button 384 may take the user 302 to a central interface/dashboard to make use of other functions of the system 110, as further described below.

In another aspect, system 110 may customize interface 302 per user 302's requirements. For example, user 302 may require ePHR share permissions to be withdrawn after a pre-determined time, when system 110 may present to user 302 an interface as described in FIG. 8A.

Figure 3C:
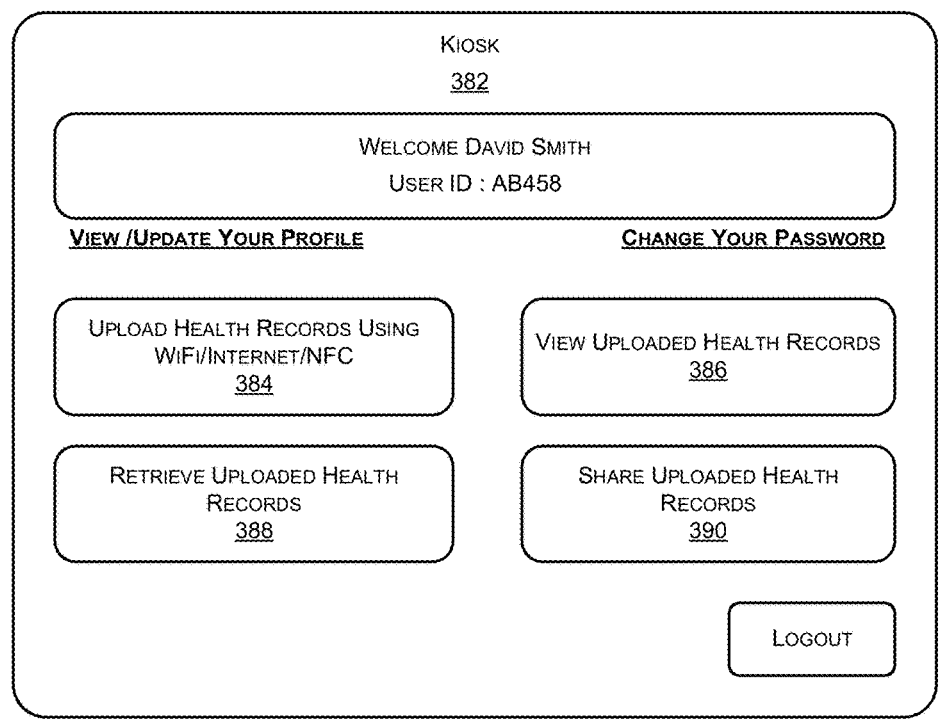
FIG. 3C shows schematic representation of a kiosk interface showing how a health record may be accessed, uploaded, stored, and shared using the system provided by the embodiments herein.

FIG. 3C, with reference to FIGS. 1 through 3B, shows schematic representation of a kiosk 382 showing how an electronic personal health record may be accessed, uploaded, stored, and shared using the system 110 provided by the embodiments herein. As shown, kiosk 382 can include an interface 380 showing user login details such as name of the user, his/her unique identifier, etc. The kiosk 382 can be configured anywhere in the public; e.g., in hospitals, healthcare offices, pharmacies, etc., wherein the interface 380 can present one or more options to a user 302 such as a portal 384 for uploading health records (e.g., ePHRs 108-1, 108-2, . . . 108-N), a portal 386 for viewing uploaded health records (e.g., ePHRs 108-1, 108-2, . . . 108-N), a portal 388 for retrieving/saving health records (e.g., ePHRs 108-1, 108-2, . . . 108-N) from a third-party system such as from a hospital database/external hyperlink to the database of the system 110, and a portal 390 for sharing uploaded health records (e.g., ePHRs 108-1, 108-2, . . . 108-N).

Figure 4:
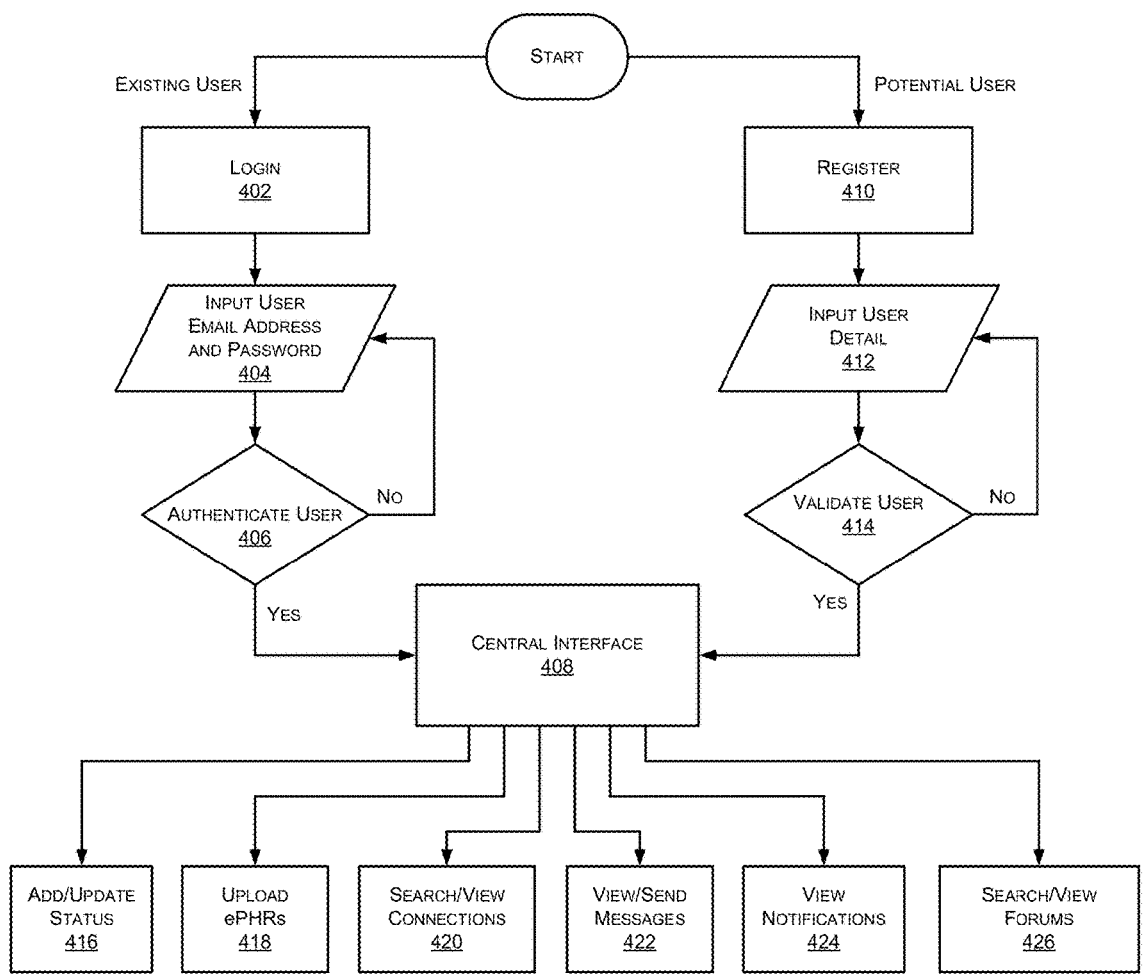
FIG. 4 is a flowchart illustrating a method according to an embodiment herein.

FIG. 4, with reference to FIGS. 1 through 3C, is a flowchart illustrating how a person may register with the system 110 and how a registered person (interchangeably termed as user 302 herein) may have access to his/her central interface (dashboard) and subsequent interfaces of the system 110 so as to make use of it.

In an aspect, all interfaces and functions being described herein may be enabled on the user's 302 computing device 324 by the system 110. The computing device 324 may be any device that may be operatively connected to system 110 using any means known in the art. For example, system 110 may be operatively connected to a website on the Internet and may be accessed by a user's Internet-enabled computing device 324. System 110 may be enabled on a Local Area Network when only such users that are granted access to the LAN may use it. The system 110 may be configured as a mobile application wherein some of modules of the mobile application may be downloaded by the user on his/her mobile device while other modules may be operatively connected to the website as described above.

In an aspect, an existing user 302 may be presented a login screen as described at block 402 when he/she intends to start using system 110. In alternate exemplary embodiments, various appropriate user interfaces such as a login screen and subsequent interfaces as described herein may be enabled on computing device 324 being employed by the user 302 to use system 110. At block 404, the user 302 may be enabled to input his/her user ID and password provided by him/her during the registration process and, after authentication as illustrated at block 406, a central interface 408 may be displayed to the user 302 on his/her computing device. In case the user 302 is not authenticated at block 406, the user 302 may be guided to repeat block 404.

In an exemplary embodiment, user ID and password may be user configurable or may be randomly generated by the system 110 and user configurable later. A user ID may be the user's e-mail address, for example. During the registration process, the e-mail address may be sent a verification link to verify a genuine user as against bots and hackers, etc., using means known in the art.

In another aspect, a user 302 (or a potential user) may be allowed a pre-determined number of login attempts (e.g., five attempts, in one example) after which he/she may be invited to recover a lost password/login ID and/or be guided to a registration interface. While using the registration interface, block 410 may initiate the process and at block 412 a potential user 302 (or someone who has lost his/her password, for example, and wants to register again) may be enabled by system 110 to provide various user details in order to make a comprehensive user profile, including user name and password. At block 414 the potential user may be validated using procedures known in the art (such as, for example, sending a verification mail to his/her computing device or a verification SMS to his/her smart phone) and, upon such validation, may be converted into an existing user and thereby granted access to central interface 408 that may be enabled upon his/her computing device 324. If validation cannot be accomplished due to any reason, the potential user may be returned to block 412. Each user 302 may likewise access his/her central interface 408. System 110 may enable the user 302 to customize the appearance of his/her central interface 408 to his/her requirements.

In an exemplary embodiment, central interface 408 and subsequent user interfaces may be automatically configured according to disability, if any, specified by the user 302 while creating his/her user profile. For example, if the user 302 is visually impaired, user interfaces for him/her may carry visual/audio aids such as bigger images, text, and audio elements to facilitate his/her usage of the system 110.

In an aspect, central interface 408 may enable several functions for the user 302. Such functions may carry their own user interfaces/APIs, as appropriate, and may be further customized by the user 302. In an exemplary embodiment, system 110 may offer functions along with enabling interfaces of add/update status at block 416, upload ePHRs 108-1, 108-2, . . . 108-N at block 418, search/view connections at block 420, view messages at block 422, view notifications at block 424, and search/view forums at block 426 via central interface 408 to a registered user 302 after he/she has logged into system 110. ePHRs 108-1, 108-2, . . . 108-N may be interchangeably termed as files. All files (ePHRs 108-1, 108-2, . . . 108-N) uploaded by the user 302 may be stored in repository 306 as allotted to the user 302, as described above. Search/view connections at block 420 may enable the user 302 to build lists of connections as described above.

In an aspect, central interface 408 may provide for various sections, in which a user 302 may post his/her status and share ePHRs 108-1, 108-2, . . . 108-N and other relevant data (such as photos) with those who are connected to him/her. Various features of the system 110 may be made available to a user 302 from his/her central interface 408, which may also be referred to herein as a "dashboard".

In various exemplary embodiments, using add/update status at block 416, a user 302 can provide a status (interchangeably referred to as "post" herein) of his/her present medical condition (or any other comment, opinion, experience, etc.) that may be viewed by other users 116-1, 116-2, . . . 116-N depending upon privacy setting for the status. The user 302 may update his/her earlier status as well. Such posts may also be provided by the user 302 in different forums that he/she may find and become members of using interface search/view forums at block 426. The post may include the user 302's ePHRs 108-1, 108-2, . . . 108-N already in his/her repository 306 and may be shared with the user 302's connections as well as external entities 118-1 including social media networks. Using interface upload ePHRs 108-1, 108-2, . . . 108-N at block 418, the user 302 may upload files such as his/her ePHRs 108-1, 108-2, . . . 108-N to his/her repository 306, and may permit another user (his/her medical practitioner, for example) to upload ePHRs 108-1, 108-2, . . . 108-N in the user 302's repository 306 for further use and sharing, as appropriate.

Using the interface at block 420, the user 302 may search for new connections (interchangeably referred to as "friends" herein) that are presently registered with the system 110. In an exemplary embodiment, to increase his/her connections, the user 302 may type the first few characters of a name (that may be, for example, as per one of his/her old friends/family name) wherein system 110 may list other existing users with the same first few characters, along with their photos. The user 302 may be able to identify his/her friend therefrom and then system 110 may enable him/her to send a connection request to the individual so identified by him/her and upon approval of the friend, add the friend to his/her connection list for friends/family. As described above, a user 302 may share his/her ePHRs 108-1, 108-2, . . . 108-N with his/her connections using various means such as text messaging. In another exemplary embodiment, using an interface at block 422 the user 302 may view messages posted on his/her central interface 408 by himself/herself and other users 116-1, 116-2, . . . 116-N so permitted by him/her.

In another aspect, using a view notifications interface at block 424 the user 302 may be provided with notifications on his/her computing device 324. Such notifications may be configured as small snippets of text and/or URLs that the user 302 may click on to get full information and may be generated either automatically by system 110 or, as required, by the user 302. For example, the user 302 may require that any status update of another user 116-1, 116-2, . . . 116-N may be notified to him/her. In such a case, a notification may be generated such that the user 302 may click on to display contents of the other user's status update on his/her (the user 302's) computing device 324. In a similar manner, notifications may be generated for the user 302 when another user 116-1, 116-2, . . . 116-N responds to a status update made by him/her, and another user 116-1, 116-2, . . . 116-N responds to a comment made by him/her in a forum, and an ePHR 108-1, 108-2, . . . 108-N is successfully uploaded by him/her, an ePHR is successfully shared by him/her, another user to whom he has sent a connection request accepts (or declines) the request, etc. In alternate exemplary embodiments, the user 302 may be enabled by the system 110 to receive other notifications.

Figure 5:
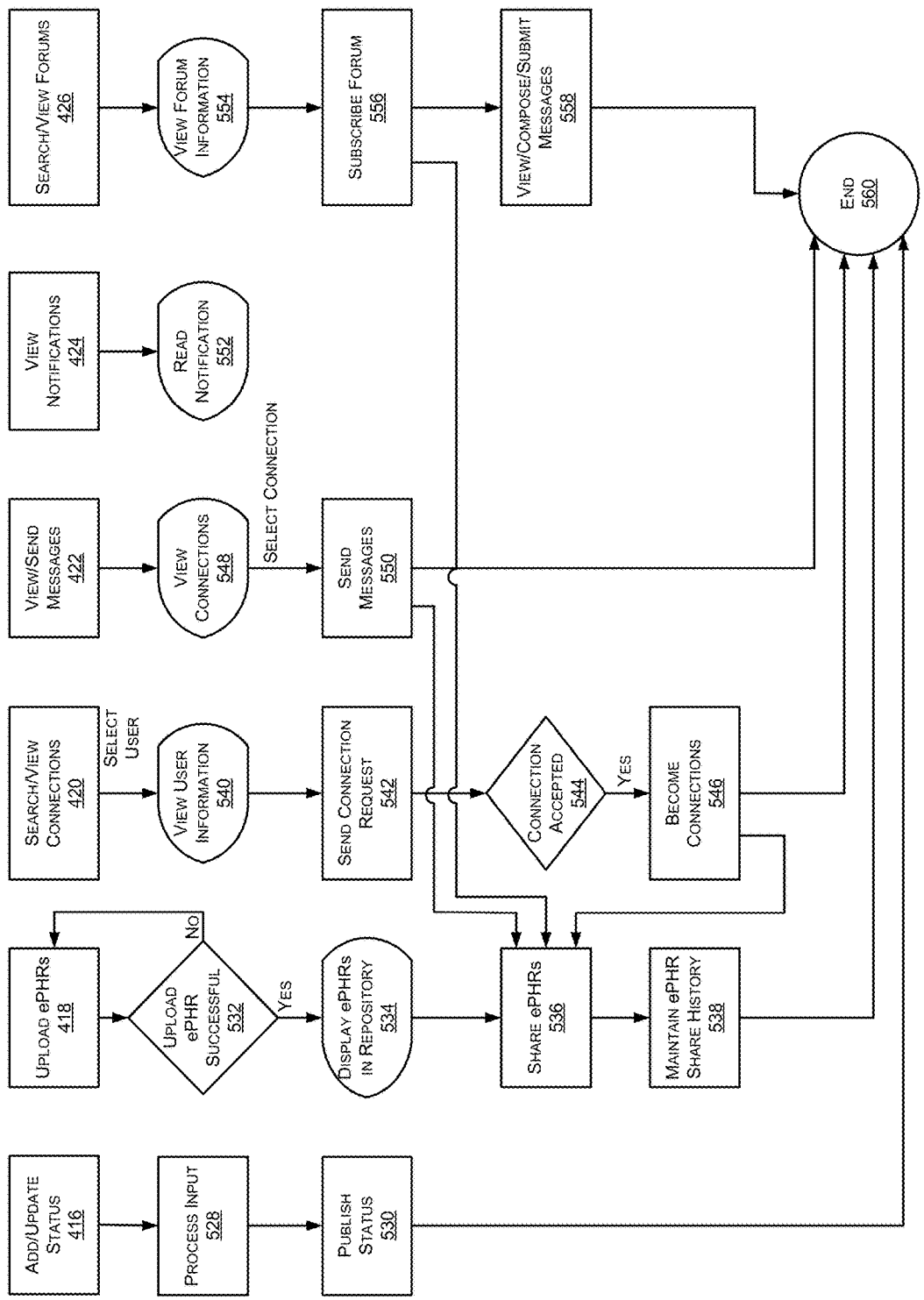
FIG. 5 is a flowchart illustrating another method according to an embodiment herein.

FIG. 5, with reference to FIGS. 1 through 4, further elaborates upon how system 110 can enable a user 302 to perform various functions that may be provided to him/her from his/her central interface/dashboard 408. In an aspect, an interface add/update status at block 416 may process the input provided by the user 302, as shown at block 528, and may then publish the user 302's status a shown at block 530. The published status may be made visible at the user 302's central interface 408 that may be configured as a webpage, for example, with different sections. The status may include photos or ePHRs 108-1, 108-2, . . . 108-N that the user 302 wants to publicly make available. In another aspect, the status may be made available to only such other users 116-1, 116-2, . . . 116-N that may be selected by the user 302, for example, a list of his/her friends/family that the user 302 can access from a corresponding list of connections. After publishing the status, the user 302 may publish another status or may choose instead to end the process, as illustrated at block 560. After ending the process, the user 302 may again be provided with central interface 408 on his/her computing device 324 so that he/she may access other interfaces and functionalities thereof.

In another aspect, interface upload of ePHRs 108-1, 108-2, . . . 108-N at block 418 may enable the user 302 to upload a file (such as an ePHR 108-1, 108-2, . . . 108-N) that may be located on his/her computing device 324 into his/her repository 306 of the system 110. The user 302's computing device 324 may be any of a computer, tablet device, a cell phone, a smart watch, a wearable device, or any computer processing device. The user 302 may drag and drop, for example, an ePHR 108-1, 108-2, . . . 108-N on an appropriate section of an interface at block 418 to upload the ePHR 108-1, 108-2, . . . 108-N. System 110 may verify whether the upload of the ePHR 108-1, 108-2, . . . 108-N has been successful and if not, enable the user 302 to repeat the process as illustrated at block 532. If the upload has been successful, the system 110 may display all uploaded ePHRs 108-1, 108-2, . . . 108-N (and their folders, if any made) in a repository 306 allotted to the user 302, as illustrated at block 534. The user 302 may further be enabled to share any ePHR or a plurality of ePHRs 108-1, 108-2, . . . 108-N as shown at block 536 and the system 110 may maintain all ePHR share histories for further use, as shown at block 538. The ePHR share history may include posts and ePHRs 108-1, 108-2, . . . 108-N shared with other users 116-1, 116-2, . . . 116-N, lists of connections or external entities 118-1 and may be used to withdraw share permissions at a later stage as required by the user 302. For example, a post may initially carry a setting of sharing with friends/family but later this setting may be withdrawn when the post may no longer be viewable by friends/family. After maintaining ePHR share history, as shown at block 538, the system 110 may enable the user 302 to upload more ePHRs 108-1, 108-2, . . . 108-N or enable him/her to choose instead to end the process, as illustrated at block 560. After ending the process, the user 302 may be again provided with central interface 408 on his/her computing device 324 so that he/she may access other interfaces and functionalities thereof.

In yet another aspect, the interface search/view connections at block 420 may enable the user 302 to search for new connections. As shown at block 540, system 110 may enable a user 302 to view information of another user 116-1, 116-2, . . . 116-N such as the other user's profile. Based upon such information, the user 302 may be enabled by system 110 to send a connection request to the other user 116-1, 116-2, . . . 116-N, as shown at block 542. If the other user 116-1, 116-2, . . . 116-N accepts the connection request, the two users 302 and 116-1, 116-2, . . . 116-N may become connections of each other, as shown at block 546. Connections can share ePHRs 108-1, 108-2, . . . 108-N, as shown at block 536 and system 110 may maintain ePHR share history, as shown at block 538. After connecting/becoming friends with the other user 116-1, 116-2, . . . 116-N, as shown at block 546, the user 302 may attempt to add more connections/friends or may choose instead to end the process, as illustrated at block 560. After ending the process, the user 302 may again be provided with central interface 408 on his/her computing device 324 so that he/she may access other interfaces and functionalities thereof.

In an aspect, the interface view/send messages at block 422 may enable a user 302 to view messages received by him/her or send messages to other users 116-1, 116-2, . . . 116-N of system 110. As shown at block 548, the user 302 may view his/her connections enabled by system 110. The user 302 may select a friend and send a message to that friend as shown at block 550. The message may enable sharing of ePHRs 108-1, 108-2, . . . 108-N, as shown at block 536 and the system 110 may maintain ePHR share history with that connection as shown at block 538. After viewing messages received or sending a message to another user 116-1, 116-2, . . . 116-N, as shown at block 550, the user 302 may attempt to view/send more messages or may choose instead to end the process, as illustrated at block 560. After ending the process, the user 302 may again be provided with central interface 408 on his/her computing device 324 so that he/she may access other interfaces and functionalities thereof.

In another aspect, the interface view notifications at block 424 may enable a user 302 to read notifications meant for him/her, as shown at block 552. Such notifications may be small snippets of text and/or URLs that the user 302 may click to get full information and may be generated either automatically by system 110 or as required by the user 302. While some examples of notifications and how they may be deployed have been described above, system 110 may enable many other types of notifications and hence, notifications are not limited only to examples described herein.

In yet another aspect, the interface search/view forums at block 426 may enable a user 302 to participate in various forums (e.g., message boards, etc.). In an exemplary embodiment, the user 302 may share a message about a medical condition or a treatment in a forum created to discuss that particular medical condition and its various treatment options. A forum may be accessible to all users, or may be restricted only to its members and likewise allow postings and discussions. System 110 may enable a user 302 to search for existing forums via search forms incorporating various search parameters wherein the search forms may either be provided by system 110 or may be built from scratch by the user 302. Any user 302 may create forums and invite other users 116-1, 116-2, . . . 116-N to participate in it, providing forum information for the purpose that may be viewed by all users, as shown at block 554. A user 302 may subscribe to a forum after viewing such information or may be invited to subscribe by another user 116-1, 116-2, . . . 116-N who is already a participant in that forum when he/she may subscribe as shown at block 556. A user 302 may subscribe to a single forum or multiple forums. After subscription, the user 302 may share any of his/her ePHRs 108-1, 108-2, . . . 108-N on the forum when such ePHR 108-1, 108-2, . . . 108-N may be viewable or downloadable by all members of the forum (per permissions set by the user 302), as shown at block 536. ePHRs 108-1, 108-2, . . . 108-N shared on forums can also be indicated in file share history, as shown at block 538. A user 302 who is member of a forum may compose and submit various messages for that forum and thereby participate in various discussions of the forum, as shown at block 558.

In an exemplary embodiment, a forum may be universal and enable discussions of any of a health-related issue, medical journal, medical topic, and a medical conference. In another exemplary embodiment, another forum may have discussions restricted based on any of a medical condition of the user 302 and his/her geographical location. In this manner, a forum can enable its member users to share information, experience, and opinions and benefit from the collected knowledge from each other.

In an exemplary embodiment, a user 302 may share his/her ePHR 108-1, 108-2, . . . 108-N on a forum and other users 116-1, 116-2, . . . 116-N may, after seeing the ePHR 108-1, 108-2, . . . 108-N, provide helpful suggestions to the user 302. Forums may be created by users who are specialist medical practitioners, for example, to provide preliminary medical advice to people suffering from the medical condition the practitioner is a specialist in. Similarly, latest advances in research and treatment of a disease, experience of a hospital, rehabilitation care and measures may all be discussed via forums. A user 302 may participate anonymously whereby other users 116-1, 116-2, . . . 116-N may not be able to see the profile of the user 302, thereby enabling total confidentiality for the user 302.

After viewing/composing/submitting messages, as shown at block 558, a user 302 may attempt to continue the process or may choose instead to end the process, as illustrated at block 560. After ending the process, the user 302 may again be provided with central interface 408 on his/her computing device 324 so that he may access other interfaces and functionalities thereof.

Figure 6:
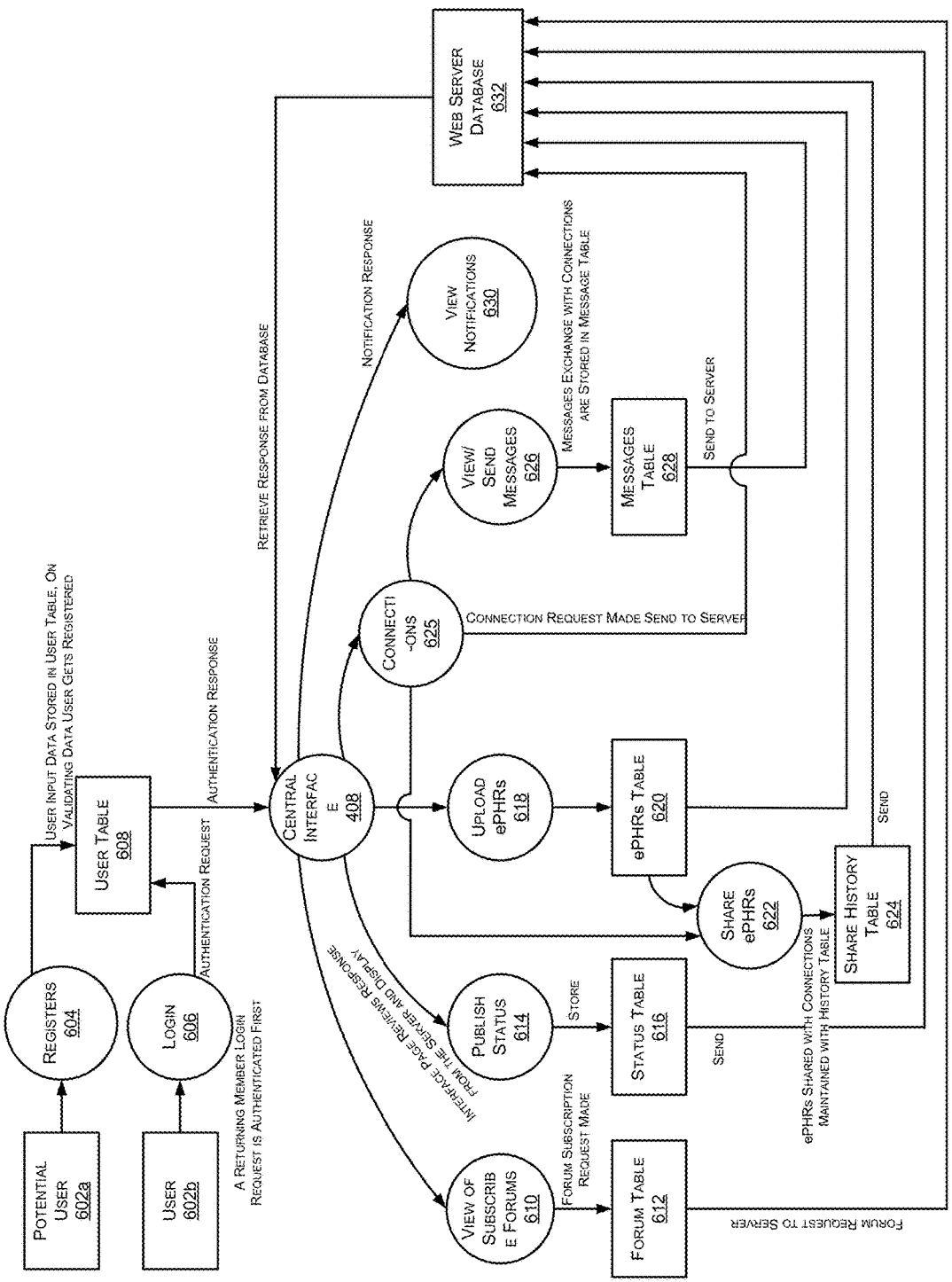
FIG. 6 is a system block diagram according to an embodiment herein.

FIG. 6, with reference to FIGS. 1 through 5, is a flowchart illustrating various data flows in the system 110, in accordance with an exemplary embodiment herein. As shown, a potential user 602a may register with the system 110 after providing various data to build his/her profile, his/her user ID and password and undergoing a validation procedure shown in the art, as illustrated at block 604. All such user data may get stored in user table 608 as illustrated and potential user 602a may get converted into actual user 602b. When user 602b tries to login as shown at block 606, his/her authorization request may be verified against user table 608 and the user 602b may be authenticated and permitted to login, using procedures known in the art. An authorization response may be issued to the user 602b and he/she may be presented with central interface/dashboard 408. The user 602b (interchangeably referred to as "only the user" herein) may access various features and functions of the system 110 from central interface 408 as described herein.

In an exemplary embodiment, the user 602b may view or subscribe to different forums as shown at block 610 and complete subscription data of the user 602b may be stored in a forum table 612 that may, in turn, be operatively connected to a database 632. In an exemplary implementation, database 632 may be configured in a web server and use the Internet to send/receive data as required. Forum table 612 may also get appropriate user data from user table 608 as required. At any time, system 110 may use forum table 612 to recognize/determine whether user 602b is subscribed to a forum or not.

In another exemplary embodiment, the user 602b may publish a status as shown at block 614. The status may be displayed on a section of central interface 408 configured, for example, like a webpage. The status of the user 602b may be stored in status table 616 that may, in turn, be operatively connected to database 632 for further retrieval, modification, and use of the status as required.

In yet another exemplary embodiment, user 602b may upload various files comprising his/her ePHRs 108-1, 108-2, . . . 108-N to his/her allotted repository 306 as shown at block 618. The repository 306 may be accessible as described above via central interface 408. All such files may be kept in a ePHRs table 620 that may, in turn, be operatively connected to database 632 for further retrieval, modification, and use of the ePHRs 108-1, 108-2, . . . 108-N as required. User 602*b* may be enabled, using system 110, to share his/her files/ePHRs 108-1, 108-2, . . . 108-N, as shown at block 622. Connections information may be received from connections block 625. A history of the shared files (ePHRs 108-1, 108-2, . . . 108-N) may be kept in a share history table 224 that may, in turn, be operatively connected to database 632 for further retrieval, modification, and use of the sharing history as required.

In an exemplary embodiment, user 602*b* may make different connections as shown at block 625. System 110 may send connection requests being made as well as responses to such connection requests to database 632. Various users 602*b* may be connected to other users 116-1, 116-2, . . . 116-N based upon connection requests and their responses, and connections of a user 602*b* may be provided via connections block 625 that may be used by user 602*b* to view his/her connections and share ePHRs 108-1, 108-2, . . . 108-N with them. Further, user 602*b* may use connections shown at block 625 to send messages to other users 116-1, 116-2, . . . 116-N and to view such messages, as shown at block 626. The messages generated by user 602*b* for his/her connections may be stored in a message table 628 that may, in turn, be operatively connected to database 632 for further retrieval, modification, and use of the messages as required.

In another exemplary embodiment, user 602*b* may view any notification as shown at block 630. Notifications may be sent by a plurality of means to user 602*b* including, but not limited to e-mail, SMS, and web-based transmission. In an exemplary embodiment, web-based notifications may be displayed to the user 602*b* on a webpage operatively connected to central interface 408.

In yet another exemplary embodiment, forum table 612, status table 616, share history table 624, ePHRs table 620, and messages table 628 may send their information to the web server database 632. In an embodiment, the central interface 408 accessible by the user 602*b* may retrieve information from the web server database 632 to display the most recent and updated information reflecting activities of the user 602*b* on a webpage operatively connected to central interface 408.

Figure 7A:
FIG. 7A illustrates a first exemplary interface of a system according to an embodiment herein.
Figures 7B, 7C:
FIG. 7B illustrates a second exemplary interface of a system according to an embodiment herein.
FIG. 7C illustrates a third exemplary interface of a system according to an embodiment herein.

FIGS. 7A to 7C, with reference to FIGS. 1 through 6, illustrate exemplary interfaces that system 110 may provide to anyone to enable them to register and become users of the system 110. In an aspect, interfaces provided by system 110 may be adapted to capabilities such as the display area of the computing device 324 a potential user may be using to register with the system 110. As illustrated in FIG. 7A, the registration interface may receive, from a potential user 602*a*, basic information such as first name 702, last name 704, email address 706, password 708, gender 712, country 714, zip code 716, city 718, and other options 720*a*, 720*b*. A potential user 602*a* may enter a password in field 708 and once again in confirm password field 710. In case there is a difference in values entered in field 708 and field 710, an appropriate message may be displayed on the display screen of computing device 234 of the potential user 602*a* and further registration process is paused until the error is rectified.

In an aspect, a potential user 602*a* may be offered free services of the system 110 and may later update to paid services with additional features. In an exemplary embodiment, a free service may offer, for example, a user 602*b* only 100 megabytes of storage space to store his/her ePHRs 108-1, 108-2, . . . 108-N while a paid service may offer 1000 megabytes of storage space to store his/her ePHRs 108-1, 108-2, . . . 108-N. In another exemplary embodiment, a free service may not have an option for the user 602*b* to ask a doctor any question while a paid service may allow for five questions a month to a doctor. In a similar manner a plurality of other paid services may be configured with respect to the system 110.

As shown at fields 720*a* and 720*b*, the registration interface may enable a user 602*b* to select options that may show on his/her profile. Such options may be enabled by a plurality of means such as check boxes, radio buttons, and free form text, for example, and may pertain to a plurality of subjects such as a medical condition, medications taken, side effects, etc. Free field options may enable the user 602*b* to enter on his/her profile any aspect of his/her medical condition for which no pre-defined options exist.

FIGS. 7B and 7C illustrate mobile registration interfaces that may be enabled on mobile devices of potential users 602*a*. As illustrated, system 110 may enable a user to provide other information as well, such as date of birth 752, interest areas 754, metros/regions resided in 756, and a biography 758. A photo may be added as shown at block 760. Also, a registration button 762 may be pressed to register the potential user 602*a* who may, after registration, be termed as a user 602*b*.

Once a potential user 602*a* has registered and become a user 602*b*, at any time he/she may login and start using system 110 by providing inputs as required by appropriately configured login interfaces. Such inputs may include his/her username, which may be his/her e-mail address, and password provided by him/her during the registration process. Additional authentication procedures such as a one-time password (OTP) to user's registered mobile number, asking him/her additional questions such as his/her date of birth, etc. may also be configured.

Figure 8A:
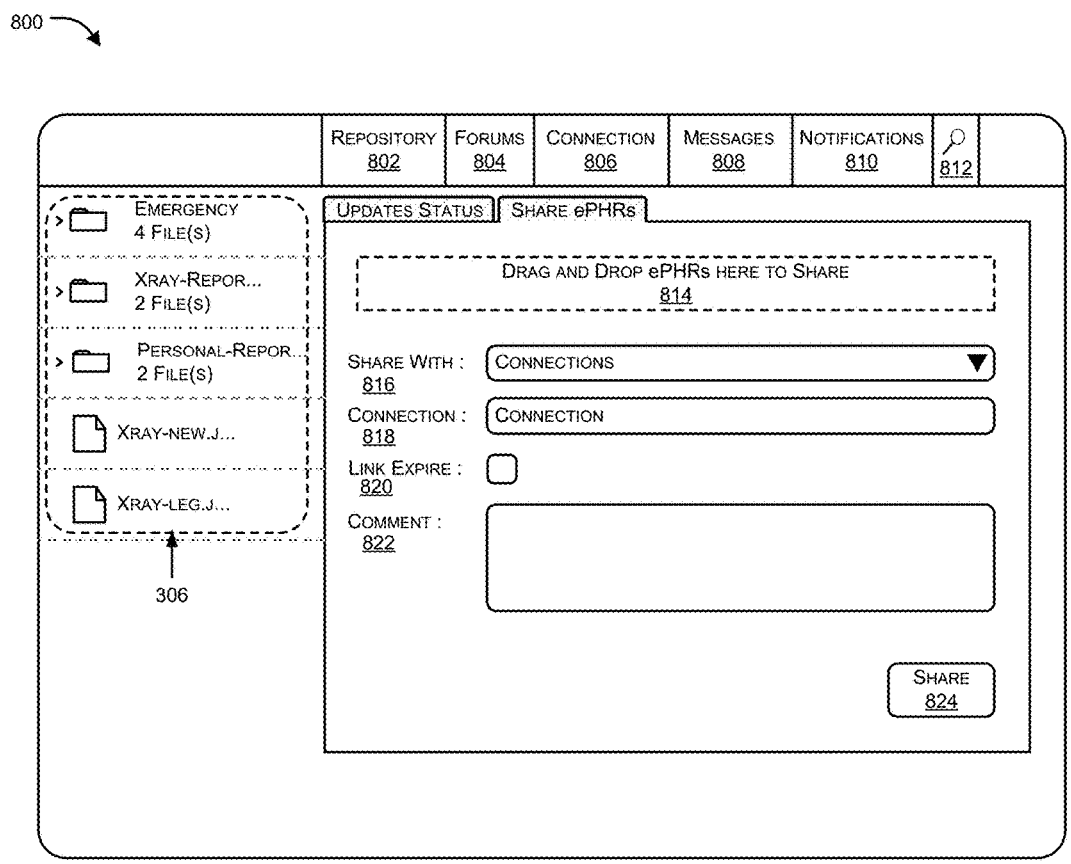
FIG. 8A illustrates a first webpage for interfacing with the system according to an embodiment herein.

FIG. 8A, with reference to FIGS. 1 through 7C, illustrates a webpage 800, which a user 602*b* may access and the central interface 408 of the system 110 provided by the embodiments herein. In continuation of FIG. 3 and FIG. 4, system 110 may provide, to user 302, a repository 306 and a central interface 408, wherein the central interface 408 may be operatively connected to a webpage 800 illustrated in FIG. 8A. Webpage 800 may have various sections and may be made available on an Internet-enabled device 324 of user 302. Using webpage 800, user 302 may have access to various functions and features of system 110. In an aspect, an interface of the webpage 800 may be completely customized by a user 302 according to his/her requirements and priorities. Such customization may include changing the color scheme, altering the order of various tabs, hiding some tabs and areas from view while increasing size of others, etc. In another aspect, webpage 800 may have various tabbed sections with labels as illustrated in FIG. 8A. Clicking on a particular tab may enable the interfaces, etc. of the corresponding function. As illustrated in FIG. 8A, the tabs may include repository 802, forums 804, connections 806, messages 808, notifications 810, and search 812.

In an example, clicking on tab repository 802 may display repository 306 of user 302 with various files and ePHRs 108-1, 108-2, . . . 108-N uploaded by the user 302 up to that time, as well as display the share ePHRs interface. In an exemplary embodiment, the share file interface may include box 814 in which the user 302 may drag and drop files containing ePHRs 108-1, 108-2, . . . 108-N to share with, in field 816, wherein the user 302 may select one of the various connection lists (such as all connections, family, friends, classmates, etc.) in order to share ePHRs 108-1, 108-2, . . . 108-N with all users in the list and select field 818 wherein the user can provide individual other users 116-1, 116-2, ... 116-N he/she wishes to share the ePHRs 108-1, 108-2, ... 108-N with. A link expiry field 820 may be provided to user 302 wherein he/she may define a date after which the sharing permissions shall be withdrawn. In an exemplary embodiment, users for which the ePHRs 108-1, 108-2, ... 108-N are to be shared with may be provided links/URLs that they may click to download the ePHRs 108-1, 108-2, ... 108-N. Such URLs may be configured to expire after a pre-determined date and such date may be provided in field 820. A comment field 822 may enable user 302 to provide comments that may be sent along with the shared ePHRs 108-1, 108-2, ... 108-N. A share button 824 may be provided and after user 302 has taken all actions required, he/she may press button 824 and thereupon, system 110 may share the ePHRs 108-1, 108-2, ... 108-N selected per requirements of the user 302.

In another aspect, tab 804 may enable, on webpage 800, forums 426 and likewise, tab 806 may enable connections 420, tab 808 may enable messages 422, and tab 810 may enable notifications 424 as described above. Tab 812 may enable user 302 to search all ePHRs 108-1, 108-2, ... 108-N, messages, connections, notifications, and forums, etc. via pre-configured templates provided by system 110 that may, in alternate exemplary embodiments, be further customized by user 302.

Figure 8B:
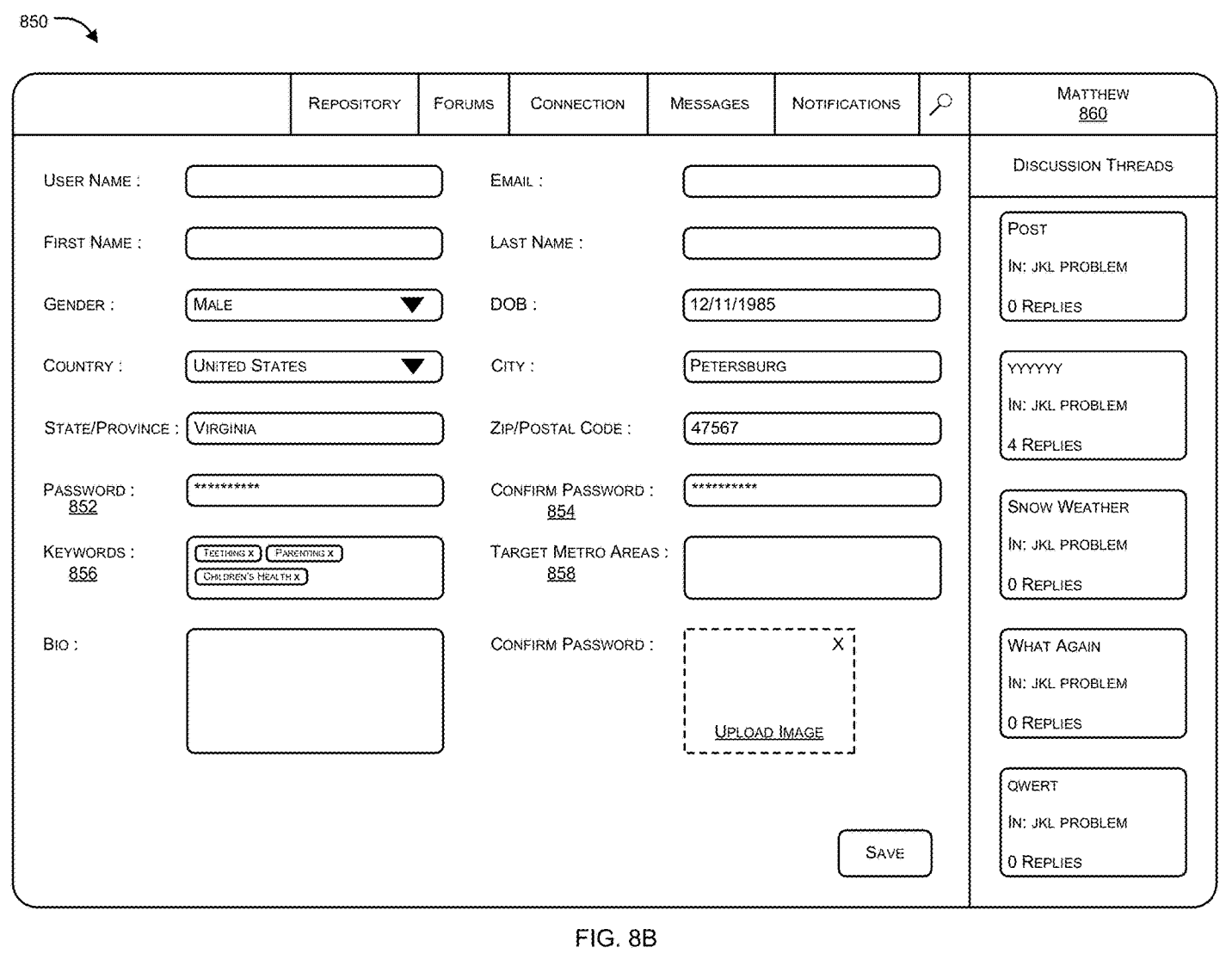

FIG. 8B, with reference to FIGS. 1 through 8A, illustrates a user profile creation interface as may be enabled on a personal computer of a user of the system 110, in accordance with an exemplary embodiment herein. A user 302, during his/her registration with system 110, may be provided an interface as shown that may lead to the creation of his/her profile page. The interface may be operatively connected to a webpage 850 as shown. Webpage 850 may collect various data and provide it to backend tables of the system 110. All personal data of the user such as his/her name, date of birth, e-mail address, location data, biodata, and photograph may be collected. Also, the user 302 may be asked to provide a password and further confirm the password as shown at fields 852 and 854. Certain keywords, as shown at field 856 as well as other information such as Target Metros as shown at field 858 may also be collected from the user 302 to enable system 110 to display relevant information. For example, with a keyword of parenting, when the user 302 searches for forums, those relating to parenting may be shown to him/her first. Likewise, when the user 302 searches for some medical practitioners in a particular region (e.g., Los Angeles, Calif.), those residing in Los Angeles, Calif. may be shown first to him/her.

In an exemplary embodiment, a user 302 may also 'pin' discussion threads of interest to him/her on his/her profile page, as shown at field 860. Such discussion threads may be extracted from those in forums the user 302 may have subscribed to and may always display on the webpage 850 of the central interface/dashboard 408 of the user 302 once the user 302 has logged into the system 110. Updates made on such threads, for example, a response to a question, may be displayed in real time on the interface webpage 850 as well, thereby enabling the user 302 to view, at a glance, various forum discussions of interest to him/her and participate in them in real time as well.

With reference to FIGS. 1 through 8B, FIG. 9A illustrates an add/update status interface while FIG. 9B illustrates a central interface of the system 110, as may be displayed on a mobile device, in accordance with an exemplary embodiment herein. In an aspect, the various interfaces of the system 110 may be adapted according to the size of the display device on which the interface displays are being rendered so as to provide the most relevant information to the user 302. As illustrated in FIG. 9A, the status update interface may provide a region 902 for a user 302 to post his/her status updates while his/her last few status updates may be shown according to display size as regions 904 and 906.

As shown in FIG. 9B, a central interface of system 110 may likewise be adapted to the size of the display to show interfaces of other functions in the form of tabs that may be clicked/touched to be expanded further. For example, the Friends (connections) tab can have intimation/notification shown as block 952 if the user 302 has received a message from a friend/connection and the user 302 may accordingly touch the Friends tab to read the message.

Figure 10A:
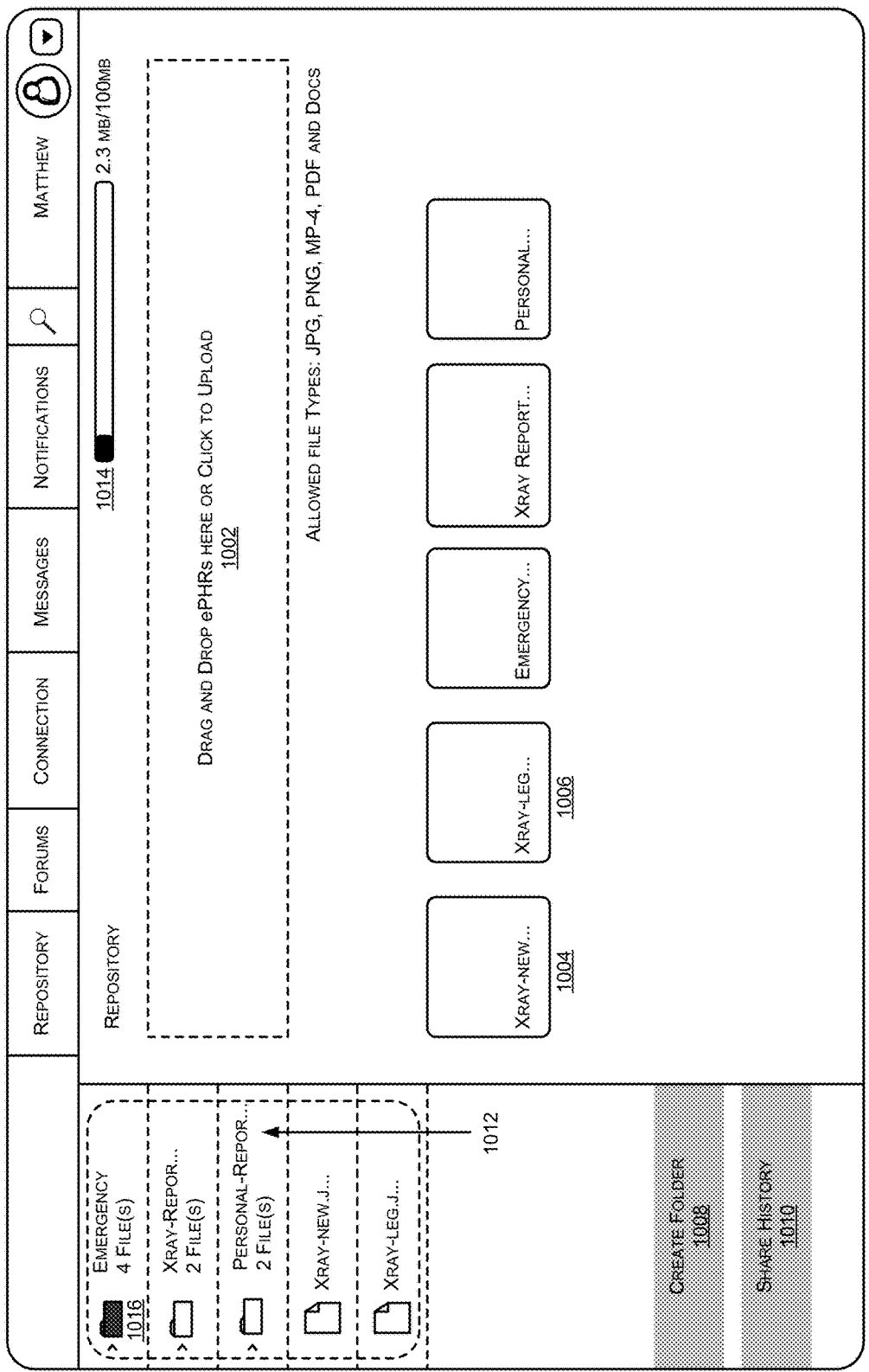
FIG. 10A illustrates a grid view of a repository containing ePHRs according to an embodiment herein.

With reference to FIGS. 1 through 9B, FIG. 10A illustrates a grid view of a repository 306 containing ePHRs 108-1, 108-2, ... 108-N while FIG. 10B illustrates a list view of the repository 306, in accordance with an exemplary embodiment herein. As illustrated in FIG. 10A, the system 110 may enable a drag and drop box 1002, wherein a user 302 may drag and drop any file (i.e., that may contain an ePHR 108-1, 108-2, ... 108-N) from his/her computing device 324 and system 110 may automatically upload it to the user 302's repository 306. After uploading, the ePHR 108-1, 108-2, ... 108-N may be tagged to provide its pointers in various folders from where it may be retrieved. Alternatively, the ePHR 108-1, 108-2, ... 108-N itself may be moved to a folder for future retrieval from that folder. ePHRs 108-1, 108-2, ... 108-N may also be uploaded to the repository 306 without being kept in any folder, as shown at blocks 1004 and 1006. ePHRs 108-1, 108-2, ... 108-N of a plurality of file formats such as jpg, jpeg, pdf, bmp, png, gif, mp3, mp4, doc, docx, xls, etc. may be uploaded and further used as described herein. ePHRs 108-1, 108-2, ... 108-N may be renamed before or after upload to better reflect their contents. The user 302 may create new folders using button 1008, and can also view the share history of any ePHR 108-1, 108-2, ... 108-N by pressing tab 1010. Various folders along with the number of files/ePHRs 108-1, 108-2, ... 108-N therein may be displayed as shown at block 1012. The user 302 may be provided a visual representation of the total storage space allotted and used, as shown at region 1014. In case the user 302 requires more storage space, he/she may upgrade to a higher service package, as described above. The repository 306 may also contain an 'Emergency' folder shown as block 1016 that may be a default folder created by administrators of system 110, wherein the user 302 may keep documents that may be helpful in case of an emergency. In an exemplary embodiment, the Emergency folder associated with block 1016 of any user 302 may be available to administrators of system 110 who may quickly access the ePHRs 108-1, 108-2, ... 108-N therein and provide them to a doctor attending to the user 302 of the system 110 in an emergency, when the user 302 himself/herself may not be in a position to access such ePHRs 108-1, 108-2, ... 108-N, or may otherwise be incapacitated. For example, the user 302 may carry a tag on his/her person with his/her user name and the phone number of the system administrators. In case of an emergency, system administrators may be contacted and they may be able to access the Emergency folder, through block 1016, of the user 302 based on his/her user ID only, and without knowing the password of the user 302. The administrators may then quickly share the ePHRs 108-1, 108-2, ... 108-N with doctors attending to the user 302.

FIG. 10B illustrates a list view of the repository 306 according to an exemplary embodiment herein. As shown, the list view may provide data such as file size 1052, type 1054, and date uploaded 1056. The list may be sorted on any of these parameters. For example, the list may be sorted based on the date uploaded parameter so as to present to the user 302 his/her latest ePHRs 108-1, 108-2, . . . 108-N first.

Figure 11B:
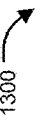

FIGS. 11A to 11E, with reference to FIGS. 1 through 10B, illustrate various interfaces pertaining to forums that may be enabled by the system 110, in accordance with exemplary embodiments herein. FIG. 11A illustrates a search interface, which a user 302 may search for forums relevant to him/her. As illustrated, the user 302 may provide, in field 1102, the topics of interest to him/her and may further provide various other search parameters such as all forums, only the forums that correspond to his/her metro areas (as may have already been specified by him/her while creating his/her user profile, as described above), forums he/she has already subscribed to, forums that may be based anywhere, and forums that are local only. The user 302 may then press search button 1104 such that the search interface may accordingly display relevant forums with the subscribe button 1106 that the user 302 may use to subscribe. The interface may also show a summary of each forum found such as its main focus (e.g., main forum block 1108), topics being presently discussed (e.g., block 1110), total number of posts (e.g., block 1112), date of last post (e.g., block 1114), and keywords that may be used to search for the forum (e.g., block 1116).

Figure 11C:
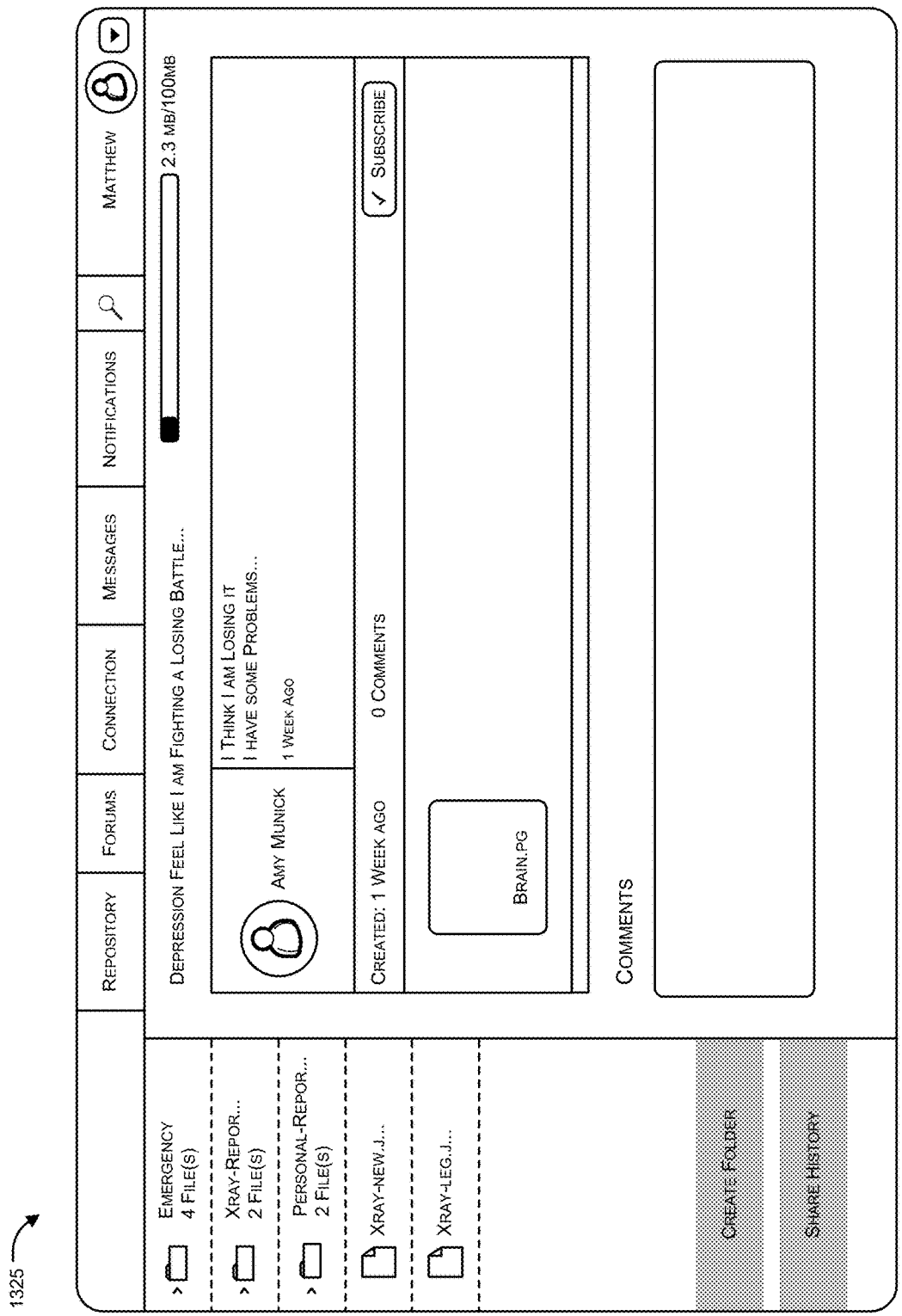

FIG. 11B illustrates a web view 1300 of a forum displaying discussion topics, according to an exemplary embodiment herein while FIG. 11C illustrates a web view 1325 of a forum displaying topic details where a user 302 may comment, according to an exemplary embodiment herein. The forum may be a public discussion area where all the users may discuss issues. As described above, a user 302 may be able to search a forum matching his/her keywords and in order to post on a forum, the user 302 may need to subscribe to that particular forum. Health records (e.g., ePHRs 108-1, 108-2, . . . 108-N) shared by a user 302 on a forum may be public and visible to all members of the forum so that forum members may discuss the medical situation of the user 302 providing such ePHRs 108-1, 108-2, . . . 108-N in an open manner.

Figure 11D:
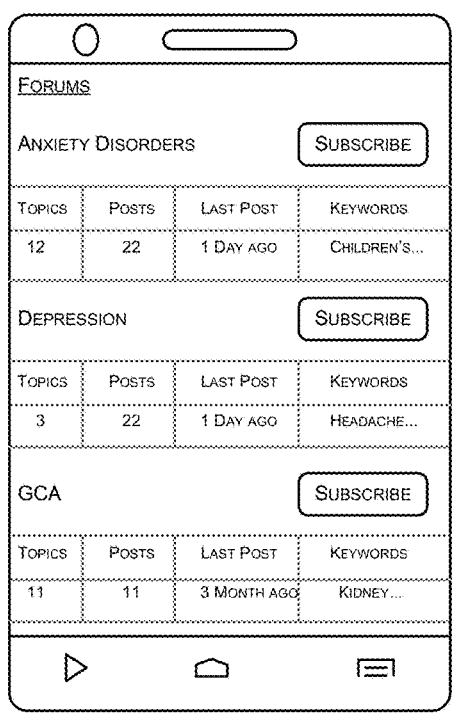
Figure 11E:

FIG. 11D illustrates a mobile view 1350 of the forum, according to an exemplary embodiment herein while FIG. 11E illustrates a mobile view 1375 of the forum with a topic screen, according to an exemplary embodiment herein. The various forum displays permit another user to provide responses, comments, opinions, "Likes", etc. to any other user's postings.

Figure 12:
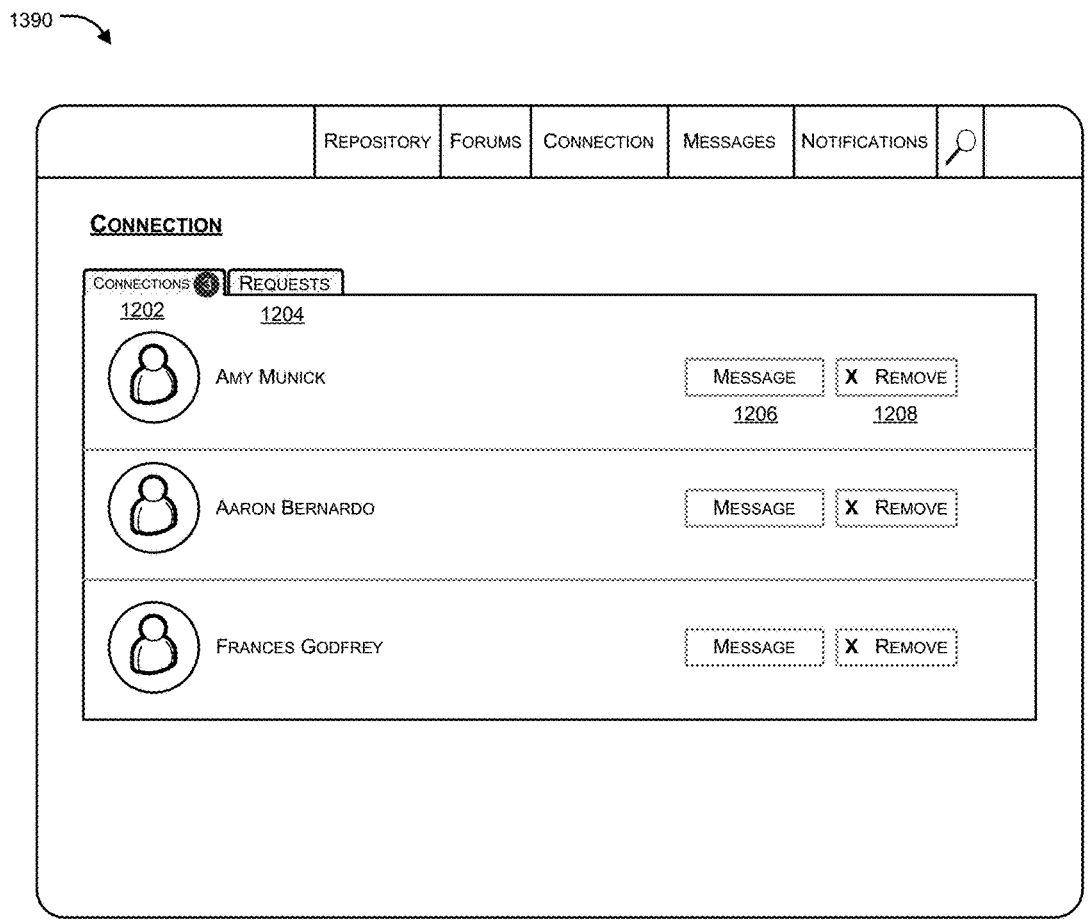
FIG. 12 illustrates a connections and connection requests interface of a user according to an embodiment herein.
Figure 13:
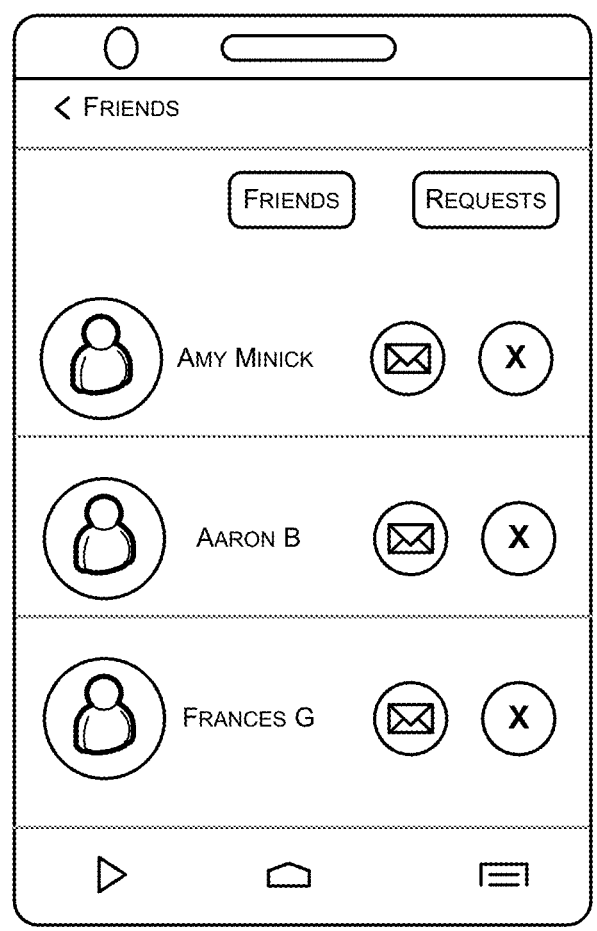
FIG. 13 illustrates a mobile implementation of an interface according to an embodiment herein.

With reference to FIGS. 1 through 11E, FIG. 12 illustrates a connections and connection requests interface 1390 of a user while FIG. 13 illustrates a mobile implementation of the same, according to exemplary embodiments herein. As shown in FIG. 12, tab 1202 may show existing connections of a user 302 each of which may be sent a message using icon 1206, or removed from the connections list of the user 302 by using icon 1208. As described above, a user 302 may increase his/her connections or friend list simply by adding other users 116-1, 116-2, . . . 116-N through various searches. In an exemplary embodiment, a user 302 may type a name in an appropriate search interface and the system 110 may show to the user 302 other users 116-1, 116-2, . . . 116-N with that name along with their photos as provided by them while creating their profile in the system 110. The user 302 may recognize his/her friend (other user) from his/her photo and send a connection request to him/her. If the other user accepts the user 302's connection request, the two users are "Connected" and may share posts, files containing ePHRs 108-1, 108-2, . . . 108-N, and may exchange messages. FIG. 13 illustrates a mobile view of the connections, according to an exemplary embodiment herein.

Figure 14:
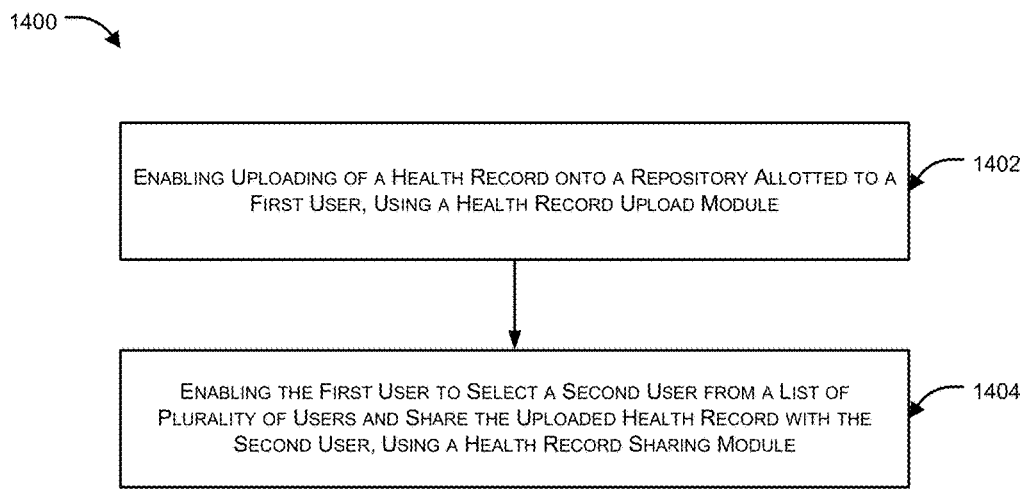
FIG. 14 is a flowchart illustrates another method according to an embodiment herein.

FIG. 14, with reference to FIGS. 1 through 13, illustrates a method 1400 of using the system 110 provided by the embodiments herein. In an aspect, block 1402 of the method 1400 may include enabling uploading of a health record (e.g., ePHRs 108-1, 108-2, . . . 108-N) onto a repository 306 allotted to a first user, using a health record upload module 204. Block 1404 of the method 1400 may include enabling the first user to select a second user from a list of plurality of users and share the uploaded health record (e.g., ePHRs 108-1, 108-2, . . . 108-N) with the second user, using a health record sharing module 206.

Figure 15:
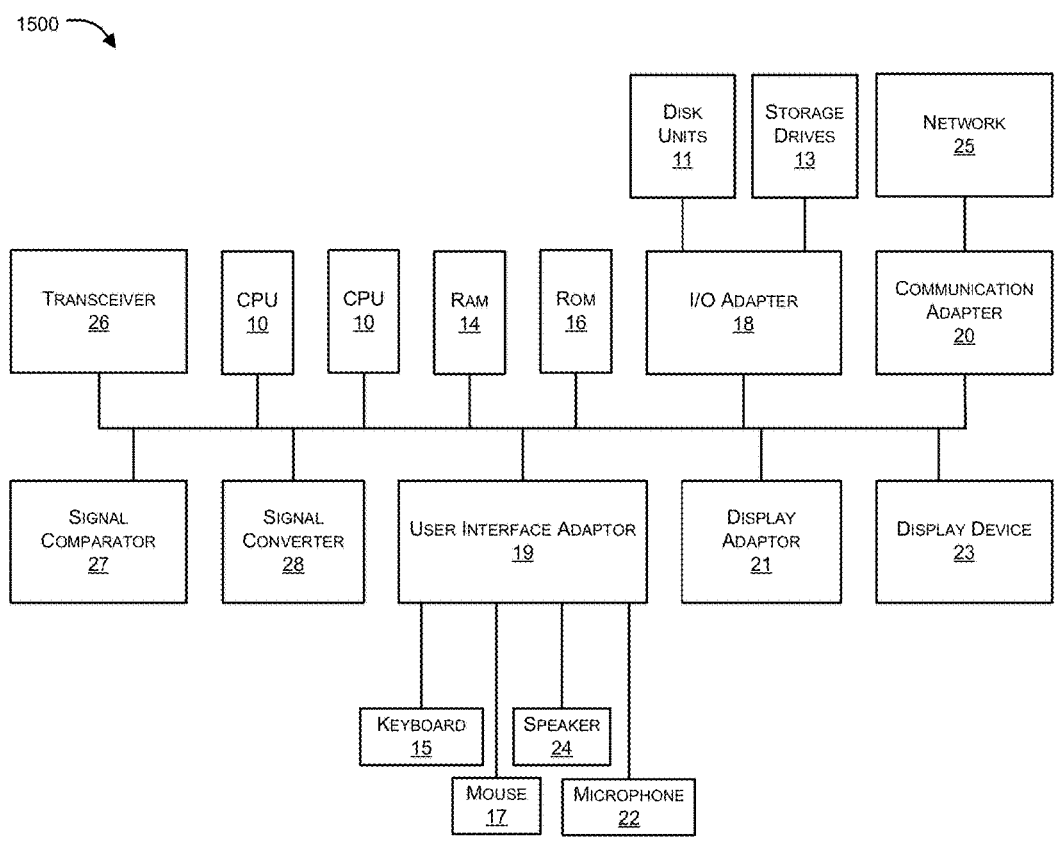
FIG. 15 depicts a hardware environment for practicing the embodiments herein.

FIG. 15, with reference to FIGS. 1 through 14, depicts a hardware environment comprising an information handling/computer system 1500 in accordance with the embodiments herein. The system 1500 comprises at least one processing device 10. The special-purpose CPUs 10 are interconnected via system bus 12 to various devices such as a random access memory (RAM) 14, read-only memory (ROM) 16, and an input/output (I/O) adapter 18. The I/O adapter 18 may connect to peripheral devices, such as disk units 11 and tape drives 13, or other program storage devices that are readable by the system. The system 1500 may read the inventive instructions on the program storage devices and follow these instructions to execute the methodology of the embodiments herein. The system 1500 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

The embodiments herein may be embodied as a computer program product configured to include a pre-configured set of instructions, which when performed, may result in actions as stated in conjunction with the methods described above. In an example, the pre-configured set of instructions may be stored on a tangible non-transitory computer readable medium or a program storage device. In an example, the tangible non-transitory computer readable medium may be configured to include the set of instructions, which when performed by a device, may cause the device to perform acts similar to the ones described here. Embodiments herein may also include tangible and/or non-transitory computer-readable storage media for carrying or having computer executable instructions or data structures stored thereon. Such non-transitory computer readable storage media may be any available media that may be accessed by a special purpose device, including the functional design of any special purpose processor as discussed above. By way of example, and not limitation, such non-transitory computer-readable media may include RAM, ROM, EEPROM, CD-ROM or other optical disk storage, magnetic disk storage or other magnetic storage devices, or any other medium which may be used to carry or store desired program code means in the form of computer executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose device to perform a certain function or group of functions. Computer-executable instructions also include program modules that are executed by computers in stand-alone or network environments. Generally, program modules include routines, programs, components, data structures, objects, and the functions inherent in the design of special-purpose devices, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips may be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product may be any product that includes integrated circuit chips, ranging from toys and other low-end applications to advanced computer products having a display, a keyboard or other input device, and a central processor, and may be configured, for example, as a kiosk 382.

The embodiments herein may include both hardware and software elements. The embodiments that are implemented in software include but are not limited to, firmware, resident software, microcode, etc. Furthermore, the embodiments herein may take the form of a computer program product accessible from a computer-usable or computer-readable medium providing program code for use by or in connection with a computer or any instruction execution system. For the purposes of this description, a computer-usable or computer readable medium may be any apparatus that may comprise, store, communicate, propagate, or transport the program for use by or in connection with the instruction execution system, apparatus, or device.

The medium may be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a RAM, a ROM, a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements may include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) may be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A communication system comprising:
   a first electronic communication device configured for transceiving electronic personal health records;
   a second electronic communication device communicatively linked to the first electronic communication device, wherein the second electronic communication device is configured for transceiving the electronic personal health records;
   a cloud-based document server communicatively linked to the first and second electronic communication devices;
   a file sharing platform communicatively linked to each of the cloud-based document server, the first electronic communication device, and the second electronic communication device, wherein digital files may be saved, accessed, and transferred to/from the cloud-based document server to the first and second electronic communication devices through the file sharing platform;
   an electronic forum communicatively linked to each of the cloud-based document server, the first electronic communication device, the second electronic communication device, and the file sharing platform, wherein the electronic forum is geographically localized based on network configurations retrieved from a global positioning system (GPS);

a communication network linking the cloud-based document server, the first electronic communication device, the second electronic communication device, the file sharing platform, and the electronic forum together;

at least one computer processor operatively linked to the cloud-based document server;

a first computer module running on the cloud-based document server, which when executed by the at least one computer processor, enables the first electronic communication device to register a computer-generated user profile, and add one or more other communication devices as electronic networked connections based on parameters comprising any of profile information, a medical condition, a geographical location, a medical practitioner, demographic attributes, and psychographic attributes;

a second computer module running on the cloud-based document server, which when executed by the at least one computer processor, enables uploading of a digital health record onto the cloud-based document server; and a third computer module running on the cloud-based document server, which when executed by the at least one computer processor, enables the first electronic communication device to select the second electronic communication device from a list of a plurality of user communication devices and share the uploaded health record with the second electronic communication device.

2. The communication system of claim 1, wherein the second electronic communication device comprises any of a communication device associated with a medical practitioner that the first electronic communication device intends to interact with, a communication device associated with a medical practitioner that the first electronic communication device has previously interacted with, a communication device associated with a user selected from a list of electronic connections of the first electronic communication device, and a communication device associated with an entity that the first electronic communication device elects to share the digital health record with.

3. The communication system of claim 1, wherein the digital health record is uploaded to the cloud-based document server by any of the first electronic communication device and the communication device associated with the medical practitioner that enables generation of the digital health record.

4. The communication system of claim 1, further comprising a web-based computer interface that enables the first electronic communication device to post to any of the file sharing platform and the electronic forum any of an electronic comment, a digital image, a computer-generated discussion topic, an update to a computer-generated user profile, an electronic message, and an electronic reply message.

5. The communication system of claim 1, wherein the uploaded digital health record is stored in the cloud-based document server in a defined computer folder in a computer file format that is implemented in the cloud-based document server.

6. The communication system of claim 1, wherein the electronic forum enables electronic discussion of any of a health-related issue, medical journal, medical topic, and a medical conference.

7. The communication system of claim 6, wherein the electronic discussion is restricted based on any of a medical condition of a first user using the first electronic communication device and a geographical location of the first user using the first electronic communication device.

8. The communication system of claim 1, wherein the uploaded digital health record comprises any of a stored and shared electronic digital health record that is communicatively transmitted from the first electronic communication device to the second electronic communication device in an encrypted format.

9. A communication system comprising:

a first mobile communication device configured for transceiving electronic personal health records;

a second mobile communication device communicatively linked to the first mobile communication device, wherein the second mobile communication device is configured for transceiving the electronic personal health records;

an electronic document repository communicatively linked to the first and second mobile communication devices;

a file sharing platform communicatively linked to each of the electronic document repository, the first mobile communication device, and the second mobile communication device, wherein digital files may be saved, accessed, and transferred to/from the electronic document repository to the first and second mobile communication devices through the file sharing platform;

an electronic forum communicatively linked to each of the electronic document repository, the first mobile communication device, the second mobile communication device, and the file sharing platform, wherein the electronic forum is geographically localized based on network configurations retrieved from a global positioning system (GPS);

a communication network linking the electronic document repository, the first mobile communication device, the second mobile communication device, the file sharing platform, and the electronic forum together;

at least one computer processor operatively linked to the electronic document repository;

a user registration module, which when executed by the at least one computer processor, enables the first mobile communication device to register a computer-generated user profile, and add one or more other communication devices as electronic networked connections based on parameters comprising any of profile information, a medical condition, a geographical location, a medical practitioner, demographic attributes, and psychographic attributes;

a health record upload module, which when executed by the at least one computer processor, enables uploading of a digital health record onto the electronic document repository; and a health record sharing module, which when executed by the at least one computer processor, enables the first mobile communication device to select the second mobile communication device from a list of a plurality of user communication devices and share the uploaded health record with the second mobile communication device, wherein the uploaded digital health record comprises any of a stored and shared electronic digital health record that is communicatively transmitted from the first mobile communication device to the second mobile communication device in an encrypted format.

10. The communication system of claim 9, further comprising a web-based computer interface that enables the first mobile communication device to post to any of the file sharing platform and the electronic forum any of an electronic comment, a digital image, a computer-generated discussion topic, an update to a computer-generated user profile, an electronic message, and an electronic reply message.

11. The communication system of claim 9, wherein the uploaded digital health record is stored in the electronic document repository in a defined computer folder in a computer file format that is implemented in the electronic document repository.

\* \* \* \* \*